(12) United States Patent
Campbell et al.

(10) Patent No.: US 11,957,618 B2
(45) Date of Patent: Apr. 16, 2024

(54) COOLING PAD

(71) Applicant: NAKK (Bowral) Pty Ltd, Frenchs Forest (AU)

(72) Inventors: Antoinette Campbell, Frenchs Forest (AU); Kylee Callow, Frenchs Forest (AU); Natalie Wearne, Frenchs Forest (AU)

(73) Assignee: NAKK (BOWRAL) PTY LTD, Frenchs Forest (AU)

(*) Notice: Subject to any disclaimer, the term of this patent is extended or adjusted under 35 U.S.C. 154(b) by 631 days.

(21) Appl. No.: 16/470,664

(22) PCT Filed: Dec. 19, 2017

(86) PCT No.: PCT/AU2017/000283
§ 371 (c)(1),
(2) Date: Jun. 18, 2019

(87) PCT Pub. No.: WO2018/112501
PCT Pub. Date: Jun. 28, 2018

(65) Prior Publication Data
US 2020/0085614 A1    Mar. 19, 2020

(30) Foreign Application Priority Data

Dec. 19, 2016    (AU) ............................... 2016905244
Aug. 22, 2017    (AU) ............................... 2017903387

(51) Int. Cl.
*A61F 7/10*        (2006.01)
*A61F 13/472*   (2006.01)
(Continued)

(52) U.S. Cl.
CPC .............. *A61F 7/10* (2013.01); *A61F 13/472* (2013.01); *A61F 2007/0021* (2013.01);
(Continued)

(58) Field of Classification Search
CPC ................... A61F 13/472; A61F 13/84; A61F 2007/0021; A61F 2007/005;
(Continued)

(56) References Cited

U.S. PATENT DOCUMENTS

| 4,397,315 A | 8/1983 | Patel |
| 5,167,655 A | 12/1992 | McCoy |

(Continued)

FOREIGN PATENT DOCUMENTS

| AU | 2011101004 A4 | 9/2011 |
| CN | 1090999 A | 8/1994 |

(Continued)

OTHER PUBLICATIONS

Extended Search Report dated Jun. 29, 2020 issued in corresponding European Application No. 17883660.7.

(Continued)

*Primary Examiner* — Tigist S Demie
(74) *Attorney, Agent, or Firm* — Nath, Goldberg & Meyer; Joshua B. Goldberg

(57) ABSTRACT

The invention provides a cooling pad 110 for alleviation of pain or discomfort, especially in the perineum as a result of childbirth. The pad 110 has at least one chamber 116 containing a fluid (such as saline) for cooling. There is at least one aperture 126 for allowing passage of body fluid. The aperture 126 is located inboard of the chamber 116. Aperture 126 is formed in a web 124.
Cooling pad 110 may be used alone or as part of an assembly, sandwiched between cover layer 130 and peel-off backing 132, and is intended to be placed in a freezer prior to use.

11 Claims, 25 Drawing Sheets

(51) Int. Cl.
- *A61F 7/00* (2006.01)
- *A61F 7/02* (2006.01)
- *A61F 13/00* (2006.01)
- *A61F 13/15* (2006.01)

(52) U.S. Cl.
CPC . *A61F 2007/005* (2013.01); *A61F 2007/0226* (2013.01); *A61F 2007/0258* (2013.01); *A61F 2007/0268* (2013.01); *A61F 2007/0285* (2013.01); *A61F 2013/00187* (2013.01); *A61F 2013/1517* (2013.01)

(58) Field of Classification Search
CPC ...... A61F 2007/0226; A61F 2007/0244; A61F 2007/0257; A61F 2007/0258; A61F 2007/026; A61F 2007/0268; A61F 2007/0285; A61F 2007/108; A61F 2013/00187; A61F 2013/1517; A61F 7/02; A61F 7/10; A61F 7/106

See application file for complete search history.

(56) References Cited

U.S. PATENT DOCUMENTS

| | | | |
|---|---|---|---|
| 5,178,139 A * | 1/1993 | Angelillo | A61F 13/84 604/389 |
| 5,304,215 A | 4/1994 | Macwhinnie et al. | |
| 5,395,399 A | 3/1995 | Rosenwald | |
| 5,476,490 A * | 12/1995 | Silver | A61F 7/03 128/890 |
| 5,679,052 A | 10/1997 | Rucki | |
| 5,697,962 A | 12/1997 | Brink et al. | |
| 8,247,637 B2 | 8/2012 | Renzin et al. | |
| 2002/0052569 A1 | 5/2002 | Horning | |
| 2005/0070980 A1* | 3/2005 | Noonan | A61F 7/02 607/108 |
| 2010/0114053 A1 | 5/2010 | Mandeville | |
| 2011/0264065 A1 | 10/2011 | Arora et al. | |
| 2011/0314640 A1 | 12/2011 | Reynolds | |
| 2012/0089106 A1* | 4/2012 | Komatsu | A61F 13/533 604/367 |
| 2012/0259303 A1* | 10/2012 | Carter | A61F 7/106 604/385.01 |
| 2013/0116762 A1 | 5/2013 | Lai | |
| 2014/0058326 A1* | 2/2014 | Cull | A61F 7/12 604/113 |
| 2014/0230825 A1 | 8/2014 | Zaltsberg et al. | |
| 2015/0080827 A1 | 3/2015 | Fogg | |
| 2016/0051404 A1 | 2/2016 | Choucair et al. | |
| 2017/0354550 A1* | 12/2017 | Park | A61F 13/5116 |

FOREIGN PATENT DOCUMENTS

| | | |
|---|---|---|
| CN | 101889920 A | 11/2010 |
| CN | 102378612 A | 3/2012 |
| JP | 2001-299807 A | 10/2001 |
| WO | 2010/114051 A1 | 10/2010 |
| WO | 2013/112175 A1 | 8/2013 |

OTHER PUBLICATIONS

Office Action dated Mar. 23, 2021 issued in corresponding Chinese Application No. 201780078742.8.
International-type search dated Jun. 16, 2017 issued in corresponding Australian Application No. 2016905244.
www.bodyice.com for BodyIce Woman breast pack retrieved from Sep. 17, 2019.
www.medichill.com.au retrieved from internet on Sep. 17, 2019.
Bodyice breast pack, www.bodyice.com retrieved from internet on Sep. 17, 2019.
Bodyice Perineum Strip, www.bodyice.com retrieved from internet on Sep. 17, 2019.
Medichillaustralia.com.au/products/medichill-cool-cubes-peri-pad-ip22-pacj-of-10, Medichill Cool Pads, retrieved from internet on Sep. 17, 2019.
Screen dump, www.medichill.com.au retrieved from internet on Sep. 17, 2019.
Screen dumps, www.bodyice.com-collections-bodyice-woman retrieved from internet on Sep. 17, 2019.
English translation of Chinese Office Action dated Dec. 16, 2021 issued in corresponding Chinese Application No. 201780078742.8.
English translation of Japanese Office Action dated Oct. 29, 2021 issued in corresponding Japanese Application No. 2019-553598.
Office Action dated Jan. 19, 2022 issued in corresponding Israel Application No. 267460.

* cited by examiner

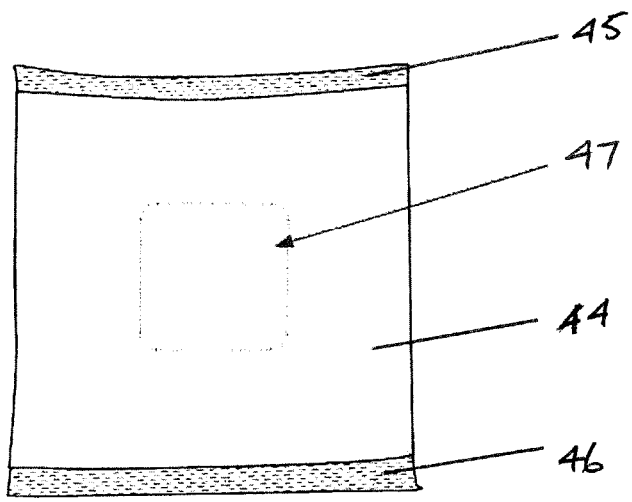
FIG 10A
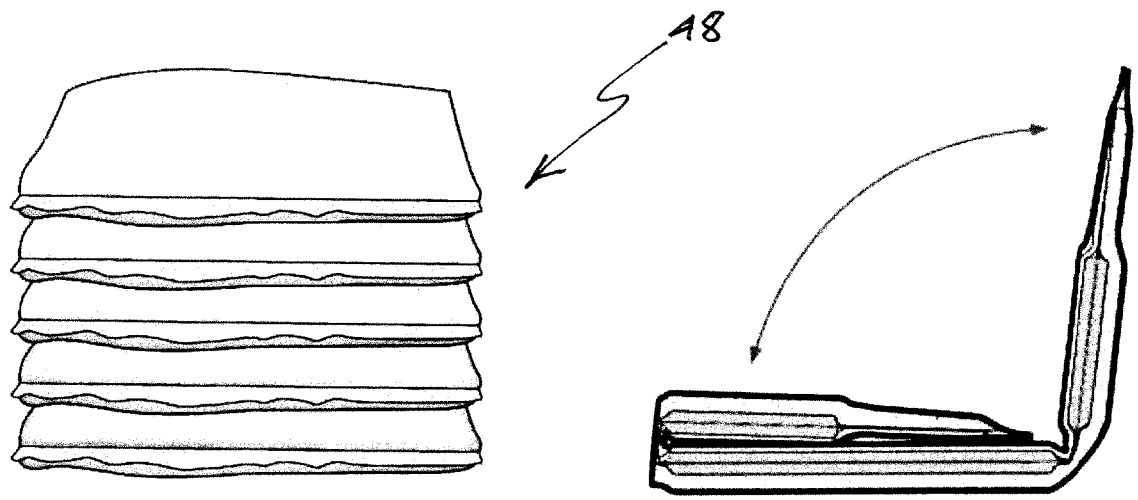
FIG 10B
FIG 10C

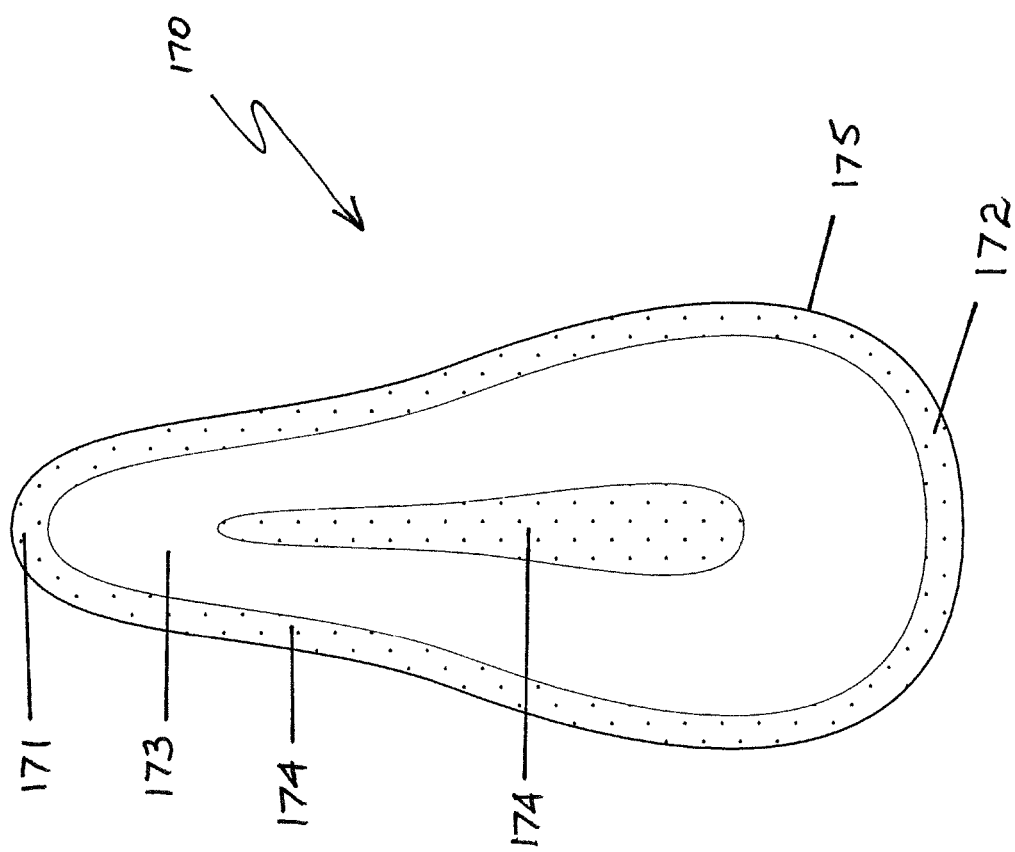

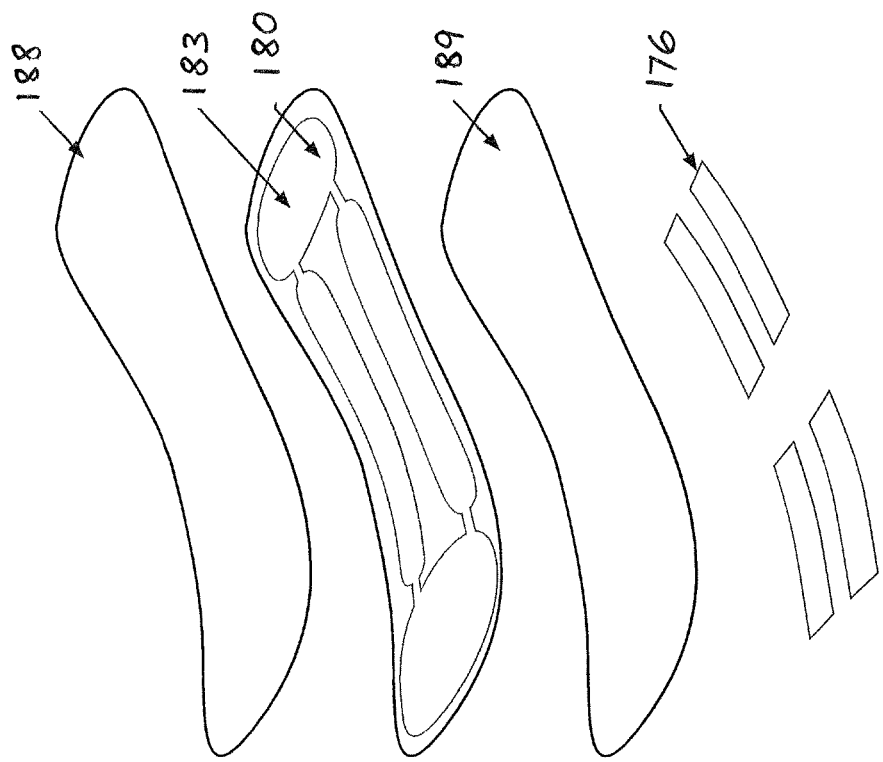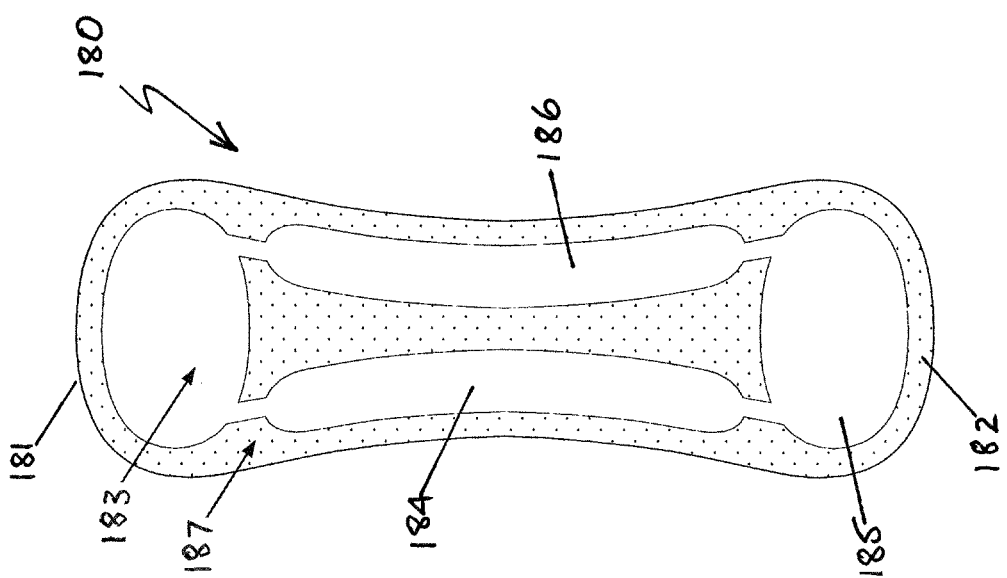

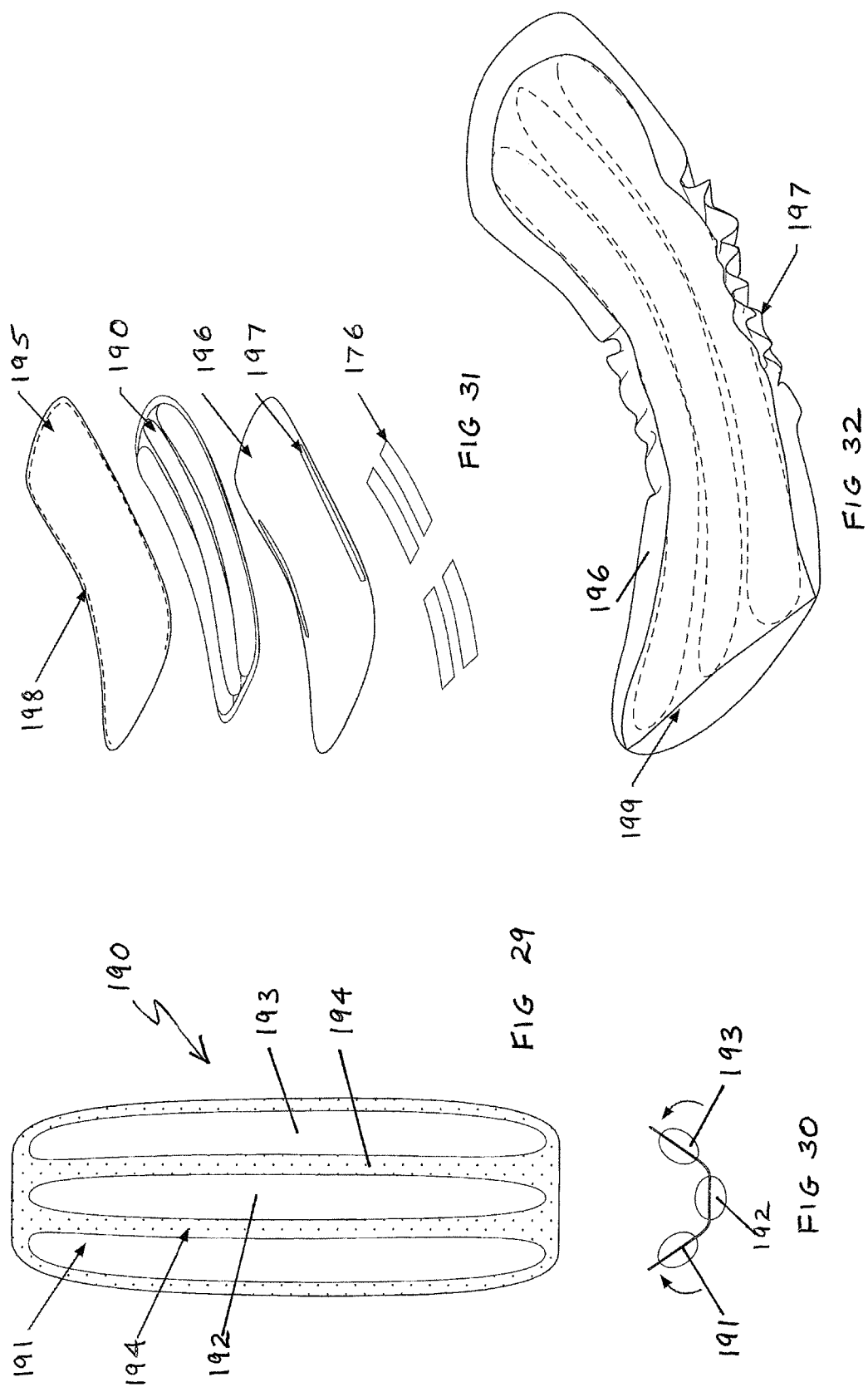

COOLING PAD

This is a National Phase Application filed under 35 U.S.C. § 371 as a national stage of International Application No. PCT/EP2017/000283, filed Dec. 19, 2017, claiming the benefit from Australian Patent Application No. 2016905244, filed Dec. 19, 2016, and Australian Patent Application No. 2017903387, filed Aug. 22, 2017, the entire content of each of which is hereby incorporated by reference in its entirety.

TECHNICAL FIELD

The invention relates to a cooling pad that in various embodiments may provide relief to the perineum after childbirth as well as in other situations, such as after vasectomy or prolonged bicycle riding or to reduce discomfort of a breast affected by mastitis. Priority is claimed of Australian Provisional patent applications 2016905244 and 2017903387, the contents of both of which are incorporated herein by reference.

BACKGROUND ART

After vaginal birth, the vaginal and perineal region can be very sore, swollen and tender. The discomfort can be significant as a consequence of acute tissue trauma.

Current practice is to use ice blocks, sometimes sheathed in rubber, as a makeshift means to provide relief. There is no satisfactory cooling device designed for treating a sore, swollen, chafed or tender perineum after vaginal birth.

Similarly, there are other circumstances in which the perineum is sore and relief is desirable. One example is discomfort experienced after vasectomy. Another example is discomfort after prolonged cycling, when chafing can occur.

A nursing mother may develop mastitis, a painful condition in which the pain caused by inflammation is exacerbated when breast-feeding an infant.

There is a need for an effective, inexpensive cooling pad which can provide relief in conditions such as those described above or which can at least provide a useful alternative.

SUMMARY OF INVENTION

Accordingly, in a first aspect, the invention provides a cooling pad for alleviation of pain or discomfort, the pad including:
  one or more chambers, containing a fluid for cooling; and
  at least one aperture for allowing passage of body fluid, the aperture being located inboard of the one or more chambers.

In one embodiment, suitable for alleviation of pain or discomfort of mastitis, the pad has a single aperture sized to accommodate a nipple. In this embodiment, it is preferred that the pad has a plurality of concentric chambers connected by webbing.

In another embodiment, suitable for perineum relief after vaginal delivery, the pad includes a plurality of the apertures for allowing passage of body fluid. Preferably, the apertures are formed in a web.

In an embodiment particularly preferred for perineum relief, the cooling pad has an anterior end and a posterior end. A chamber, containing the fluid for cooling, has a first volume at the anterior end and a pair of second volumes between the anterior end and the posterior end. A web between the pair of second volumes has a plurality of the apertures to allow passage of body fluid.

In this embodiment, it is preferred that the pad has a single chamber as described. Preferably, the chamber is in a roughly horseshoe configuration, with the first volume located at the head of the horseshoe and the second volumes located in the legs of the horseshoe. There is an opening between the ends of the horseshoe, the ends being located at the posterior end of the pad.

It is preferred that the first volume is presented as having a large surface area, whereas each of the second volumes has a smaller surface area. The first volume may form a continuous chamber with the pair of second volumes.

When the web has a plurality of apertures, it is preferred that there are several apertures, such as five, and that the apertures are of a size to allow body fluids to flow through the cooling pad with no or little restriction. In one embodiment, each aperture is generally oval in shape, having a length of between 1.5 and 2.5 cm and a width of up to 1 cm. It is preferred that the apertures are located at spaced intervals, for example from the first volume to the end of the second volumes and of differing sizes. In this embodiment, one or more apertures closer to the first volume are preferably larger than apertures towards the end of the second volumes. The apertures may be graduated in size along the web.

In a second aspect, the invention provides a cooling pad for perineum relief, the pad having an anterior end and a posterior end, and including one or more chambers, containing a fluid for cooling, located on a web.

The invention in the second aspect is particularly suitable for use as a cycle pad or a prostate pad, where the passage of body fluid is not involved.

In the aspects of the invention, it is preferred that the chamber or chambers are at or near the periphery of the cooling pad. The chamber or chambers do not need to be continuous around the periphery or to travel around the whole periphery. However it is preferred that the chamber or chambers travel around a substantial part of the periphery.

The pad may have any desired shape. For example, when used after vaginal delivery, the pad may be a generally elongated oval or may have a shape similar to a maternity pad. For this application, the pad may have a wider anterior end and a narrower posterior end. When used for mastitis, the pad may be circular. When used as a cycle pad, the shape may be that of a teardrop. For a prostate pad, the shape may be generally rectangular.

For both aspects of the invention, each chamber may be round or ovoid in cross-section, or any other suitable shape.

For both aspects of the invention, the cooling fluid may be any suitable fluid. In one preferred embodiment, the cooling fluid is a saline solution, which may contain an amount of innocuous dye to tint the solution to a desired colour, such as aqua. The saline solution may include an anti-bacterial to enhance shelf life. As other examples, the cooling fluid may be water, another non-toxic solution or a gel.

The cooling fluid may be cooled in a freezer or refrigerator as required. Alternately, the cooling fluid may be of a type which does not require freezing: the fluid may comprise urea and an inner water-filled tube which, when broken, causes an endothermic reaction with the urea, resulting in cooling.

Preferably, the chamber size and number and the type of cooling fluid are designed to provide cooling relief for up to about 30 minutes after extraction from a freezer or refrigerator. Once the cooling fluid has reached a temperature at which the pad is no longer effective in providing relief, the pad may be discarded.

There may be a plurality of chambers segmented between at least two of front, middle and rear sections. In this embodiment, fold lines may delineate the sections. The chambers are preferably segmented between all three of the front, the middle and the rear sections. The chambers of the front and rear sections are preferably shaped and oriented in a facing horseshoe configuration. It is preferred that the horseshoe-shaped chamber of the rear section is larger than the horseshoe-shaped chamber of the front section, and has a further discrete chamber (preferably teardrop-shaped) centred within.

Conveniently, the cooling pad of the invention may be formed by heat-sealing two layers of suitable sheet plastic, forming the chamber and the web in one step. The cooling pad of the invention may be formed in any other suitable way.

The cooling pad of the invention may be used alone, or it may be inserted into a suitable pocket for use. In another embodiment, the cooling pad of the invention may be combined with one or more layers in an assembly, to add comfort or to enable adhesion to clothing or a pad, for example.

For instance, a cover layer may be placed over and adhered to the cooling pad, to provide an interface between the cooling pad and the relevant part of the perineum or other body part. The cover layer should allow body fluid to flow through in an appropriate application. The cover layer may be contoured to fit the body of the user. The cover layer may be impregnated with botanical or other products to aid healing or to provide a pleasing fragrance. If desired, the cover layer may incorporate wings with adhesive on one side, for adhering the cooling pad and cover to a garment.

The cooling pad of the invention may include one or more adhesive strips to enable the cooling pad to be adhered to the body, to underwear or to a pad for absorbing body fluid. A peel-off backing may protect the adhesive until the cooling pad is ready for use. The adhesive strips may be located in any desired position on the cooling pad, but preferably under the cooling pad in use.

The cooling pad of the invention in its various aspects may have on it or on its packaging a temperature-sensitive device printed or embedded thereon. Such a device can indicate when the cooling pad of the invention is sufficiently cool to be ready for use.

BRIEF DESCRIPTION OF THE DRAWINGS

The invention will now be described in relation to non-limiting embodiments, in conjunction with the accompanying drawings, in which:

FIGS. 10A to 10C are schematic representations of packaging forms for the embodiments depicted in connection with FIGS. 1 to 9;

FIG. 26 is a plan view of an embodiment of a cycle pad according to the invention;

FIG. 27 is a plan view of another embodiment of cycle pad according to the invention;

FIG. 28 is an exploded view of the cycle pad of FIG. 27 in an assembly;

FIG. 29 is a plan view of an embodiment of a prostate or vasectomy pad according to the invention;

FIG. 30 is a side view of the embodiment of FIG. 29;

FIG. 31 is an exploded view of the prostate pad of FIG. 29 inserted into an assembly; and FIG. 32 shows the assembly of FIG. 31.

DESCRIPTION OF EMBODIMENTS

Several embodiments are presented herein, some of which have variant constructions. None is intended to be limiting on the scope of the invention.

Figure 1:
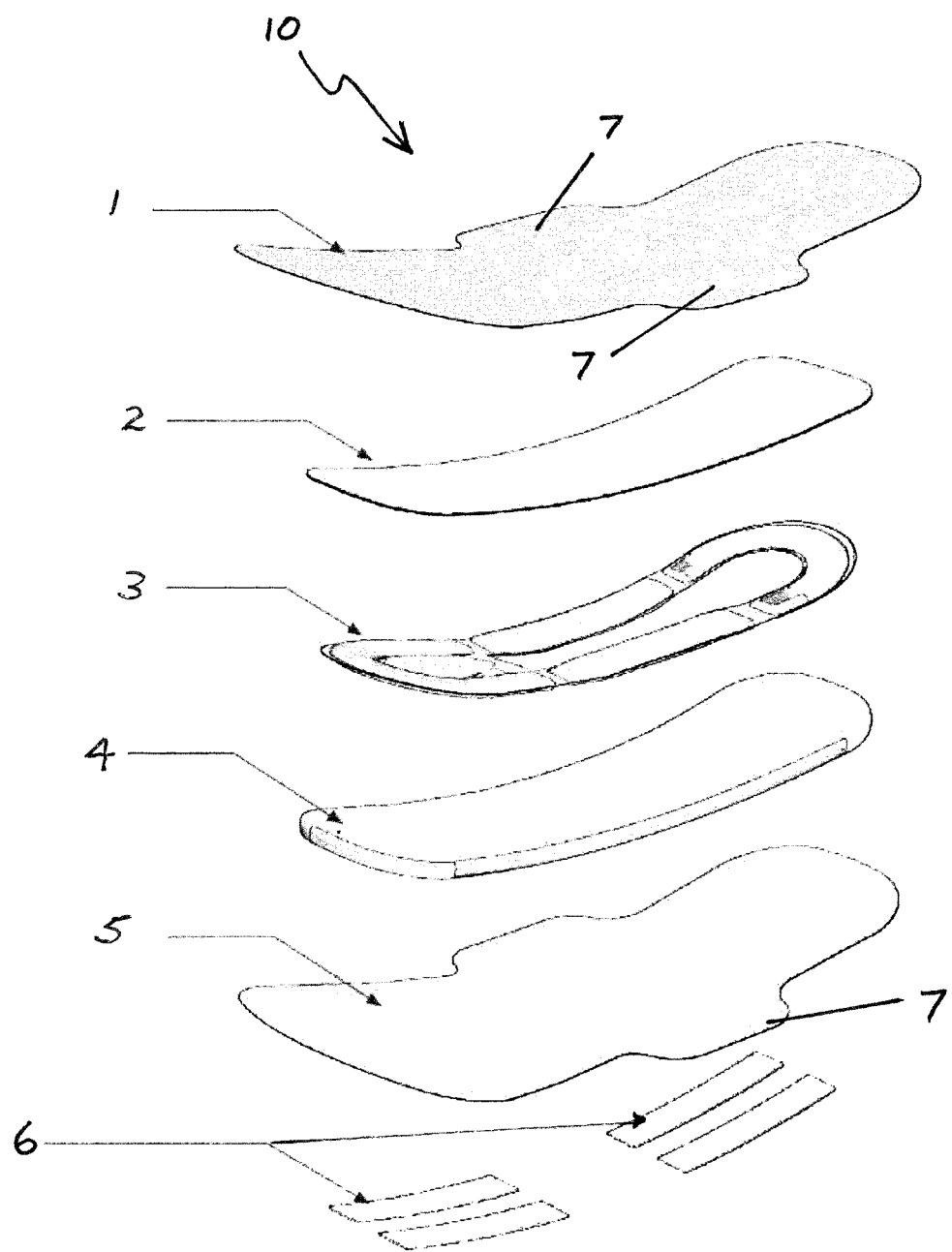
FIG. 1 is an exploded view of components of a cooling pad assembly according to a first embodiment of the present invention, which is packaged as a winged pad in assembled form.
Figure 2:
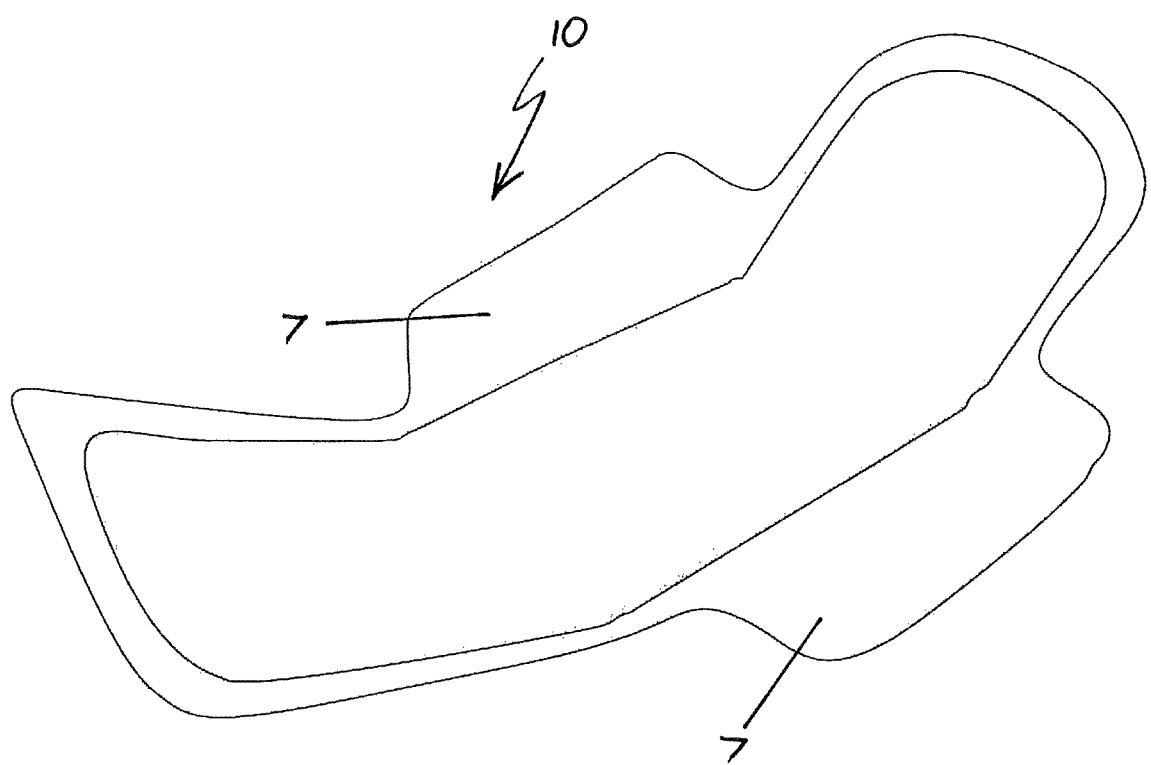
FIG. 2 is a perspective view of an assembled winged pad housing the components of FIG. 1.

FIGS. 1 and 2 present a first embodiment of a winged version of cooling pad assembly in exploded and assembled view. FIG. 1 conveys the assembly and layers of the construction. FIG. 2 depicts the final constructed assembly of this embodiment.

The assembly 10 depicted in FIG. 1 is for a single use disposable pad assembly. The assembly 10 comprises a soft and thin absorption layer 1, intended for contact with skin, a thin absorption layer 2, optionally impregnated with one or more of witch hazel and lavender, to aid in wound healing, a cooling pad 3 to aid in relieving discomfort and help healing from swelling, perineal tears and episiotomies, a super absorbent core layer 4 to absorb fluids, an impermeable bottom layer 5 for increased protection from body fluids and adhesive strips 6 to keep pad in place.

Layers 1 and 5 include wings 7.

Cooling pad 3 is described in more detail in connection with FIG. 6, below.

Figure 3:
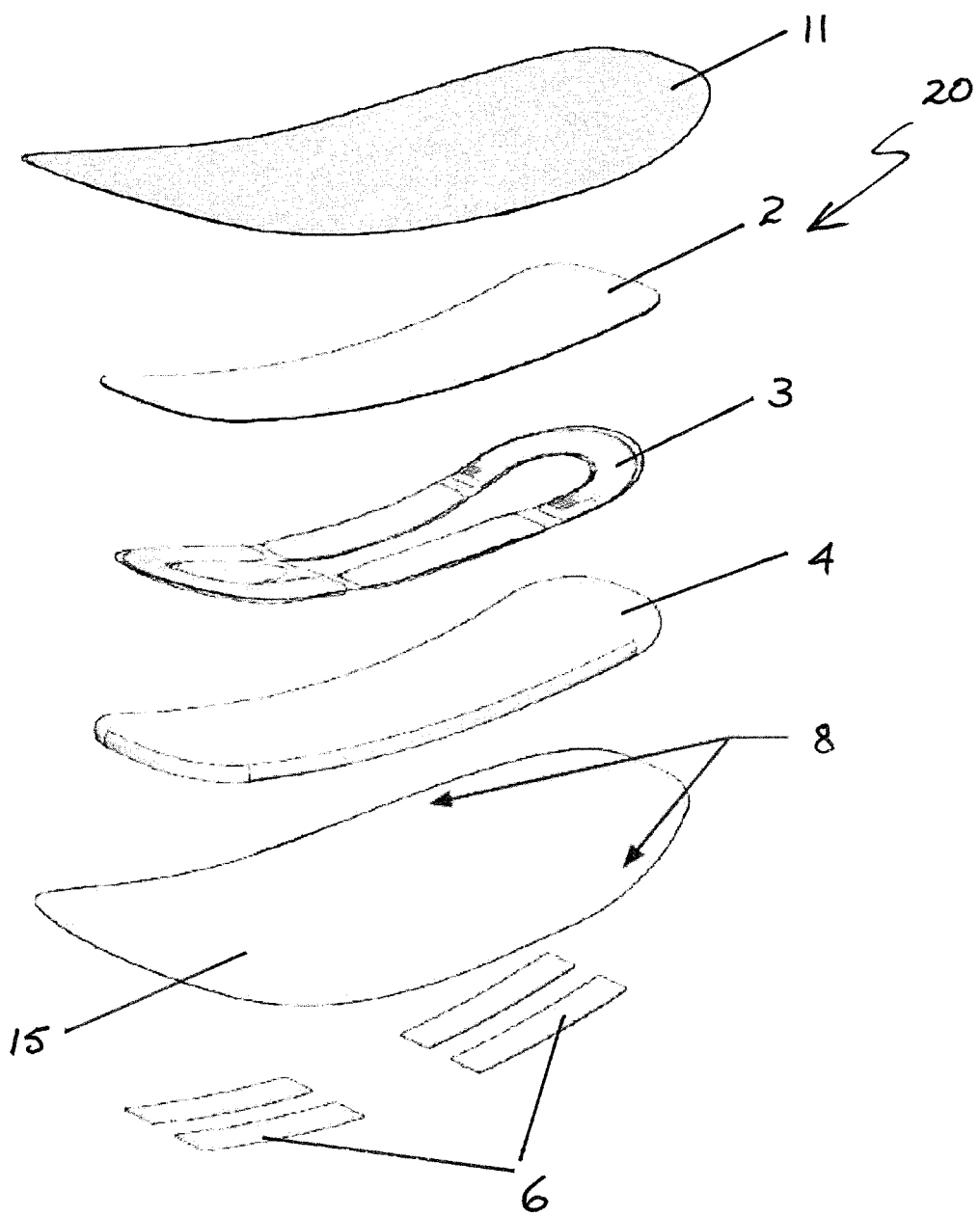
FIG. 3 is an exploded view of components of a cooling pad assembly according to a second embodiment of the present invention, which is packaged as an elasticised pad in assembled form.
Figure 4:
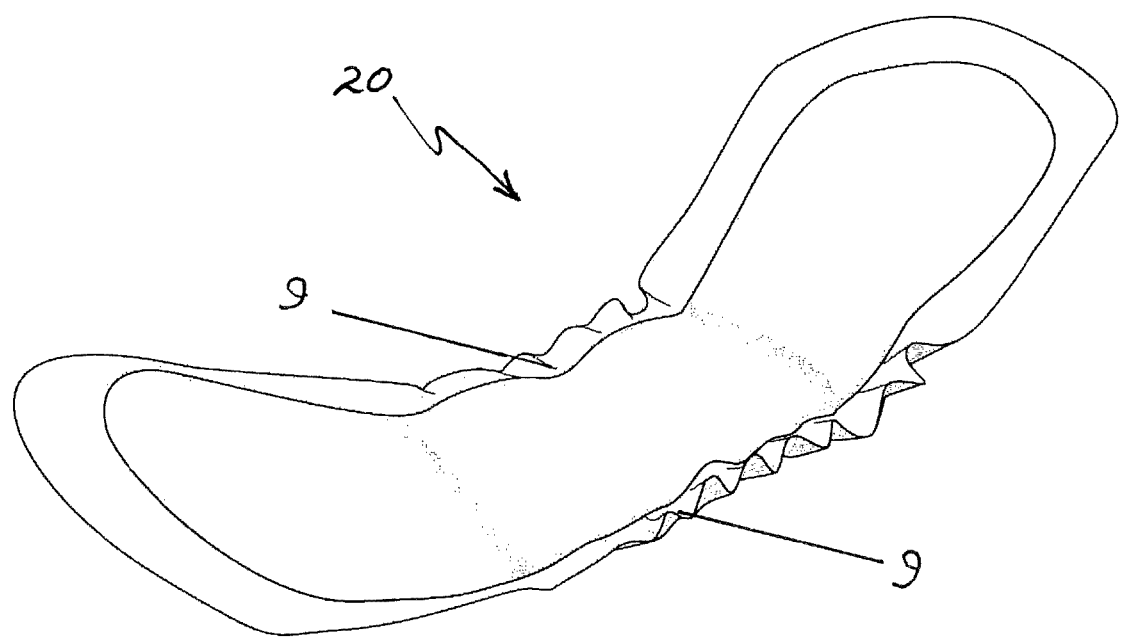
FIG. 4 is a perspective view of an assembled elasticised pad housing the components of FIG. 3.

FIGS. 3 and 4 present a second embodiment of an elasticised version of cooling pad assembly 20 in exploded and assembled view.

Items being the same as in FIGS. 1 and 2 carry the same labels.

The assembly 20 depicted in FIG. 3 is also for a single use disposable pad assembly. The assembly 20 comprises a soft and thin absorption layer 11, intended for contact with skin, a thin absorption layer 2, optionally impregnated with one or more of witch hazel and lavender, to aid in wound healing, a cooling pad 3 to aid in relieving discomfort and help healing from swelling, perineal tears and episiotomies, a super absorbent core layer 4 to absorb fluids, an impermeable bottom layer 15 for increased protection from body fluids and adhesive strips 6 to keep pad 20 in place.

FIGS. 3 and 4 are analogous to FIGS. 1 and 2, as is apparent. Most layers are the same, barring minor changes in shape to avoid a winged footprint. A notable difference is that impermeable bottom layer 5 features elasticised strip ribbing 8, to result in an assembled pad with elasticised sides as evident in FIG. 4, instead of the wings 7 in FIGS. 1 and 2. Elasticised sides 9 are designed to fit snugly to protect against leakage and provide a comfortable fit.

Figure 5:
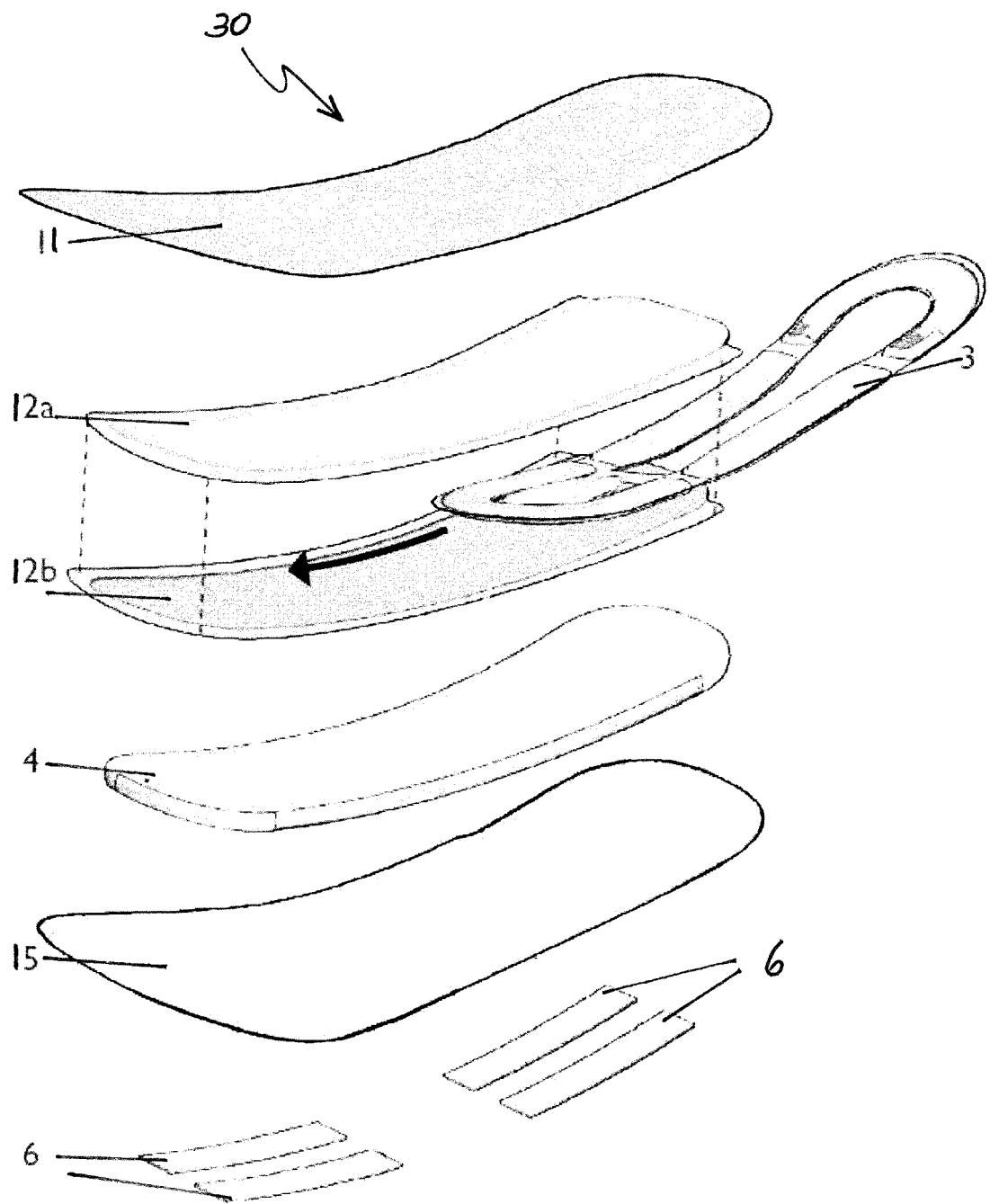
FIG. 5 is an exploded view of components of a cooling pad assembly according to a third embodiment of the present invention, which is a variation of the first embodiment.
Figure 6:
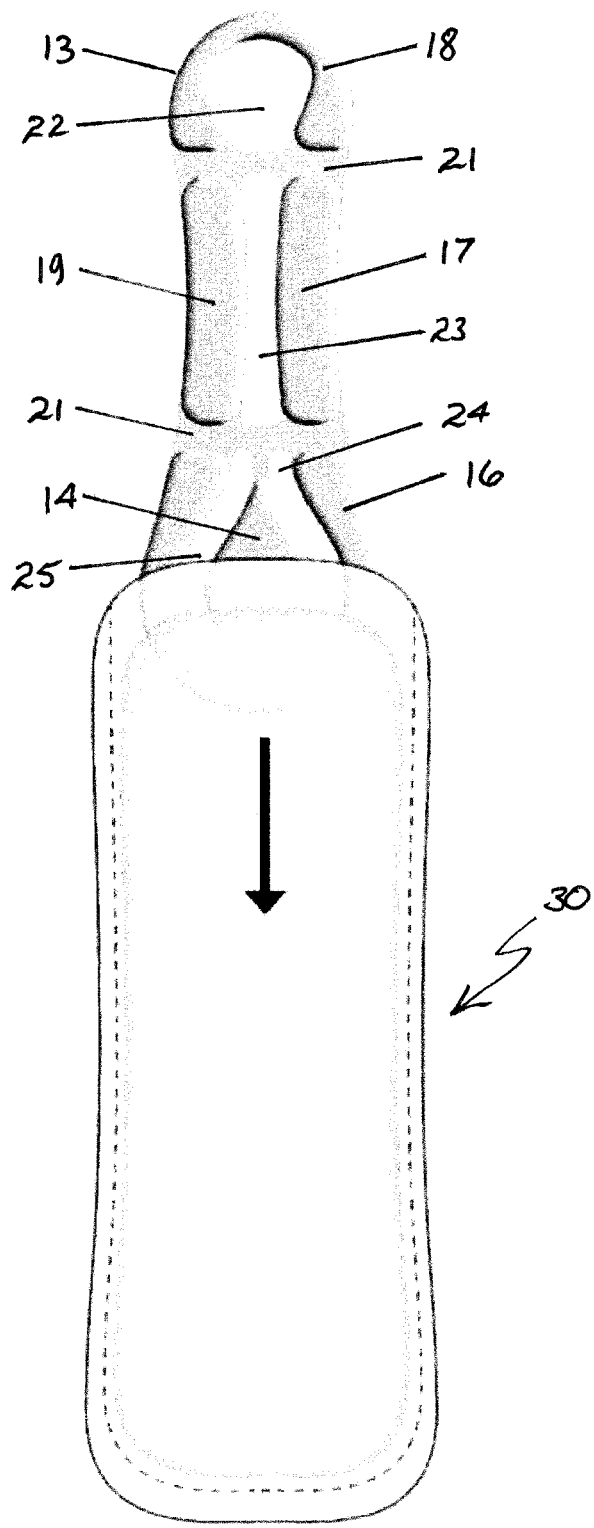
FIG. 6 is a plan view of a cooling pad assembly of FIG. 5.

FIGS. 5 and 6 depicts in exploded view and detail components forming a variation to the first and second embodiments in which a "pocket" option is an alternative to the fully assembled construction outlined described and illustrated in connection with FIGS. 1 to 4.

FIG. 5 shows this alternative assembly 30. Layers 11, 4, 15 and 6 are essentially identical to the second embodiment described above in connection with FIGS. 3 and 4, omitting elasticised ribbing 8.

Thin absorption layers 12a and 12b are fused together with an opening at the top to allow cooling pad 3 to be inserted later. Layer 12b covers and is bonded to bottom layers 4, 15 and 6. This alternative is illustrated as wingless but could have wings as in FIGS. 1 and 2 or elasticised sides as in FIGS. 3 and 4.

The benefits of this alternative include that cooling pad 3 is inserted only if needed, and that cooling pad 3 can be supplied separately, instead of as part of an assembly.

As can be seen in FIG. 6, cooling pad 3 has a periphery indicated at 13 and includes an inboard chamber 14 as well as chambers 16, 17, 18 and 19 around periphery 13. Each chamber 14, 16, 17, 18 and 19 contains a fluid for cooling, being a saline solution.

Chambers 14, 16, 17, 18 and 19 are joined by web 21, which also contains apertures 22 to 25, for passage of body fluid to super absorbent core layer 4. Apertures 22 to 25, are located inboard of chambers 16, 17, 18 and 19.

Figure 7A:
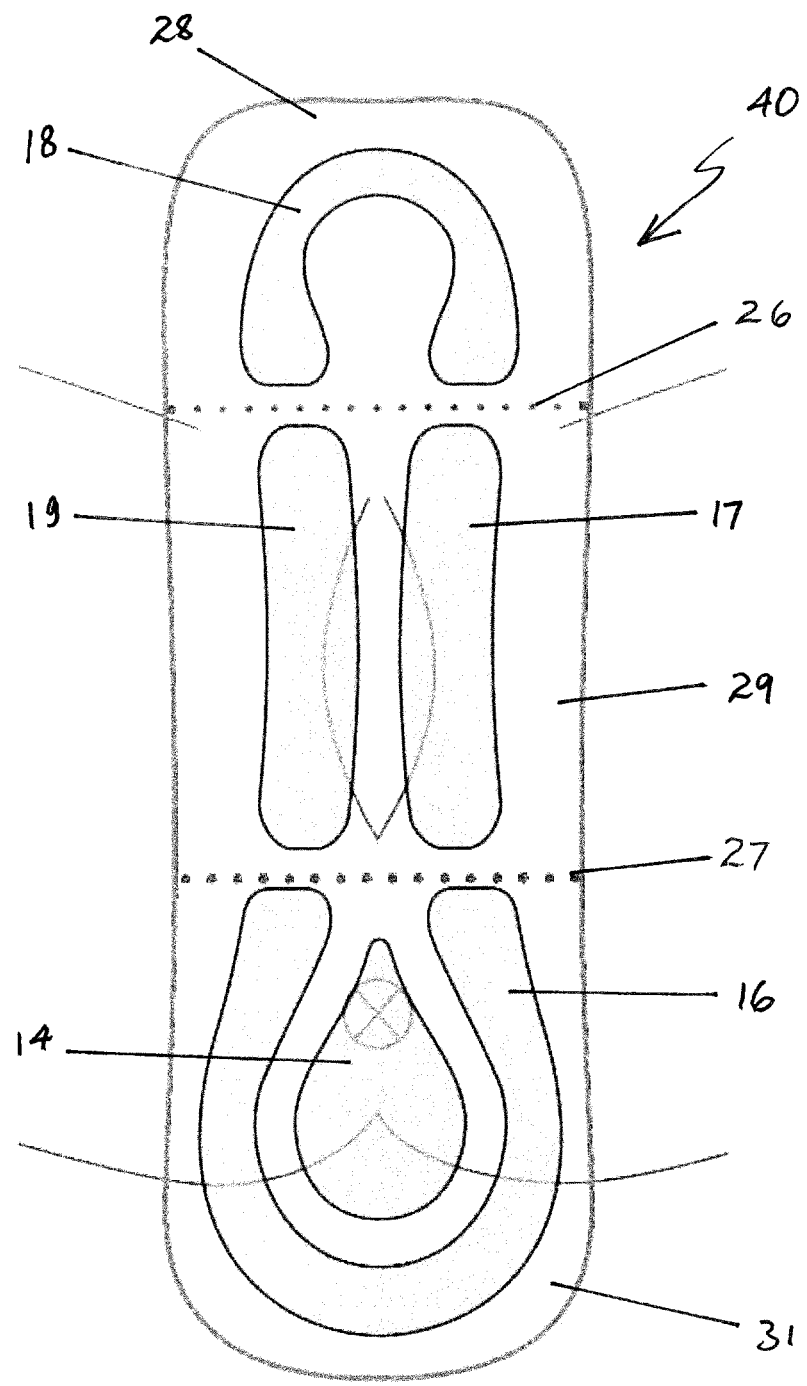
FIGS. 7 to 9 are schematic representations of respective variations in cooling pad design, and able to be used with first, second and first embodiments, of cooling pad assembly, overlayed with anatomical and nominal dimensional data.
Figure 7B:
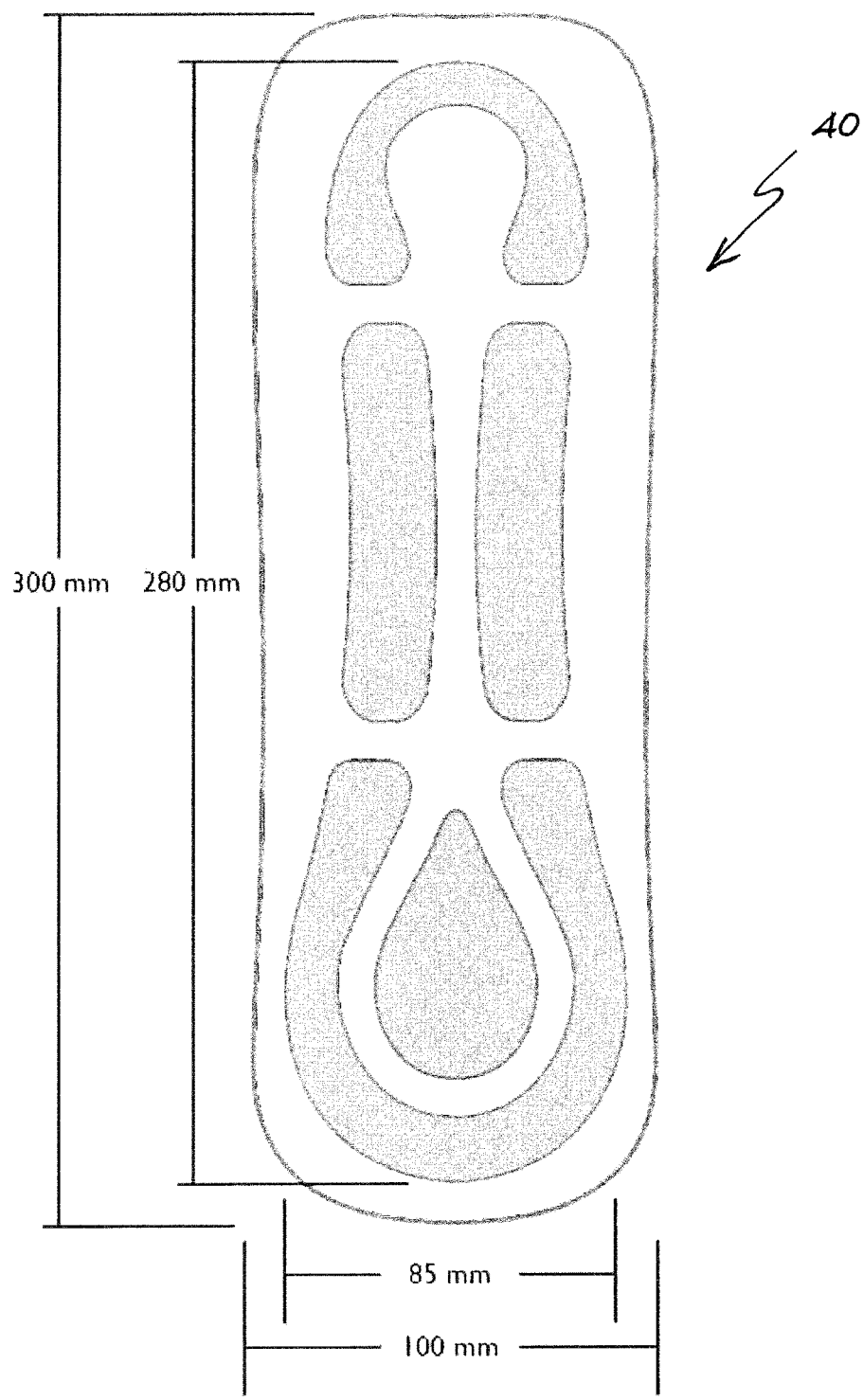
Figure 8A:
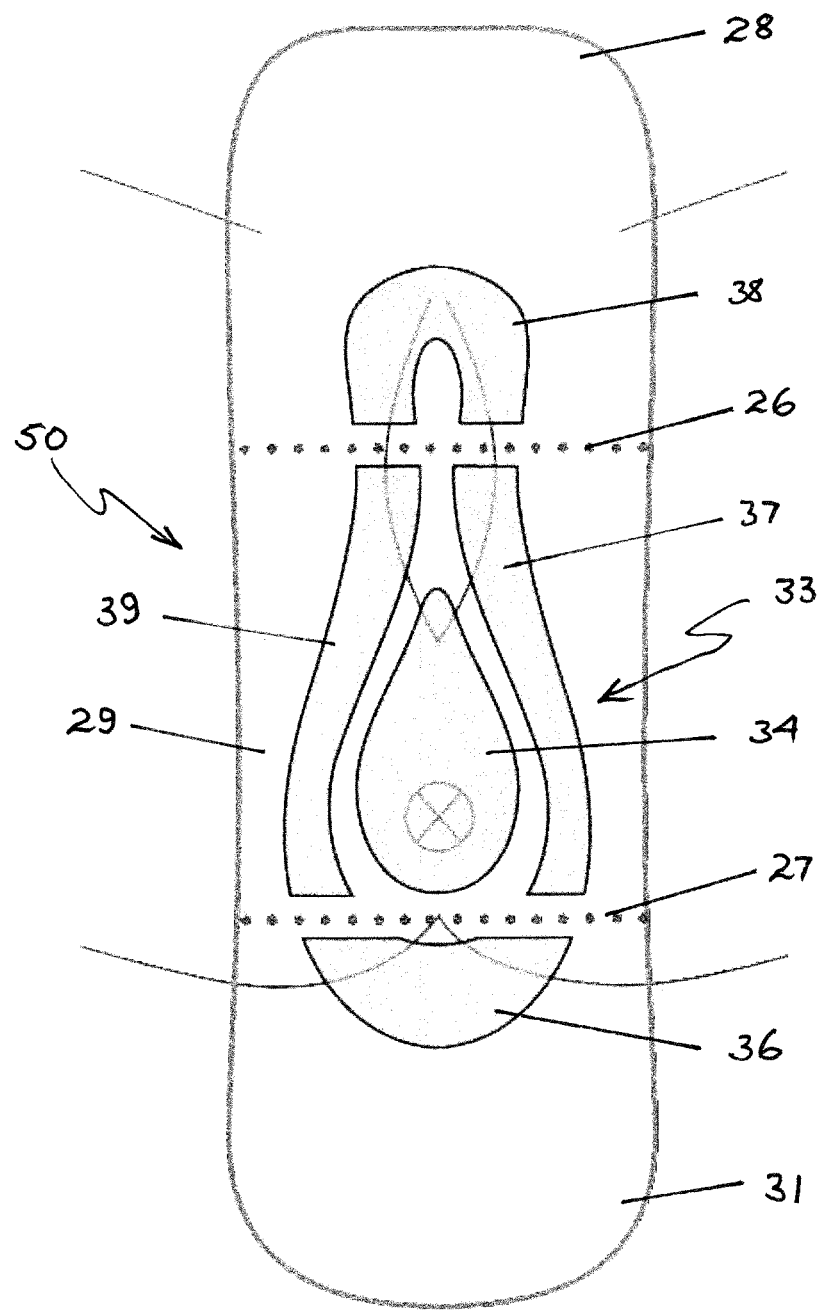
Figure 8B:
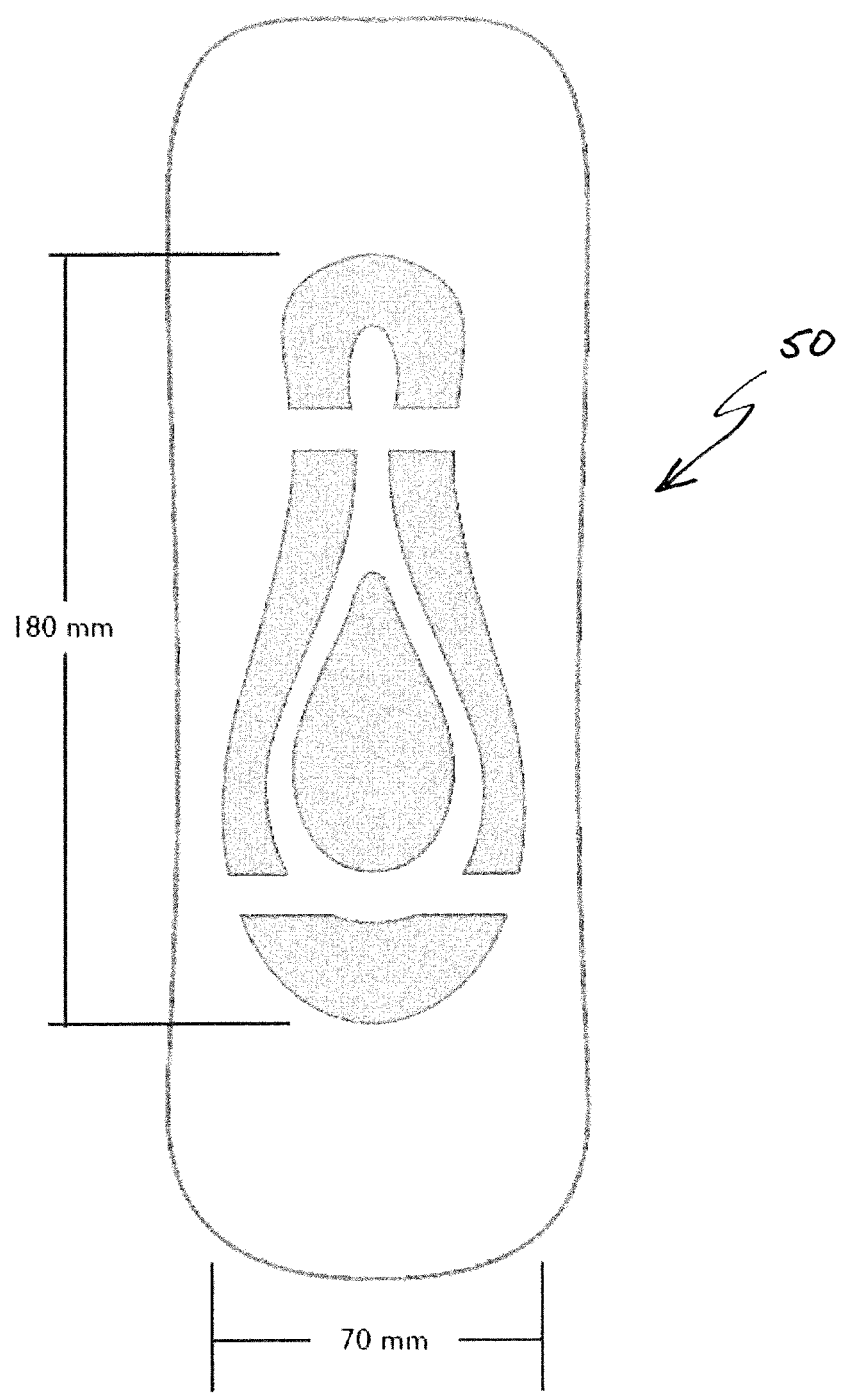
Figure 9A:
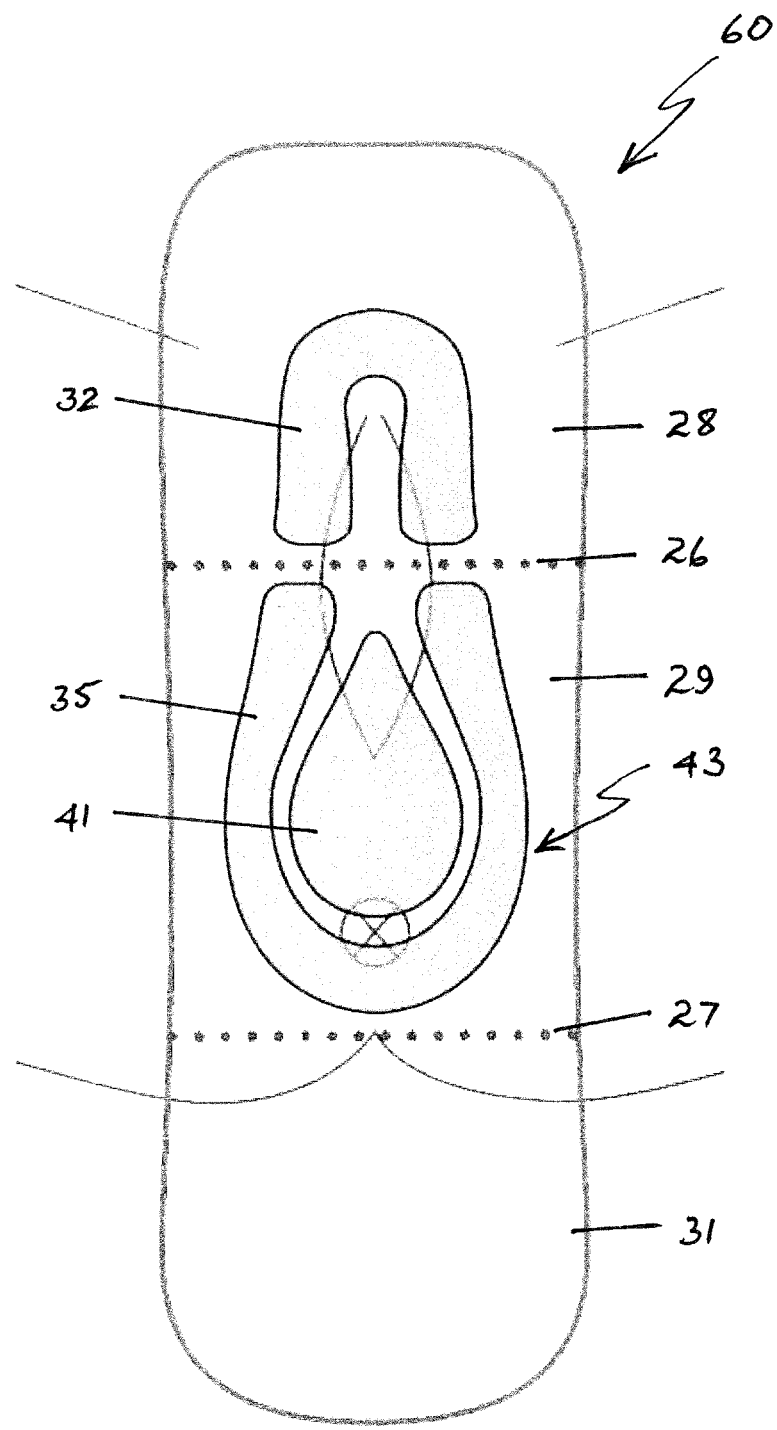
Figure 9B:
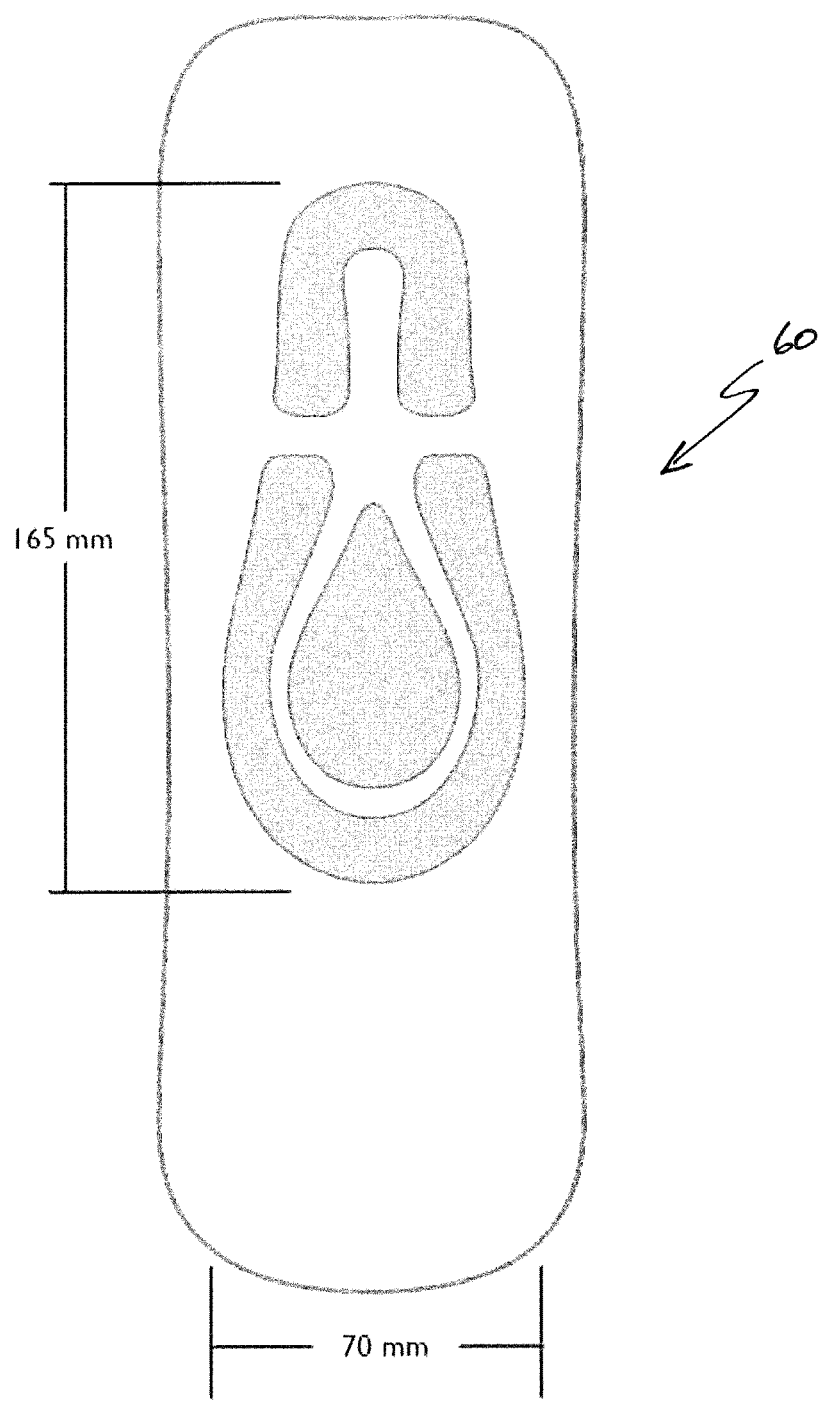

FIGS. 7A-9A present three cooling pad assembly variations, with FIGS. 7B, 8B and 9B presenting matching nominal dimensions for these three variations. In each of FIGS. 7 to 9, cooling pad 3 is visible for purposes of illustration, although in fact cooling pad 3 would be covered by at least two layers.

In FIG. 7A, cooling pad 3 is shown in situ as part of an assembly 40, which is similar to assembly 10 (omitting wings 7) or assembly 20 (omitting elasticised sides 9). For simplicity, web 21 is omitted Superimposed on assembly 40 is a schematic of the main areas of the perineum, showing location of assembly 40 in use. Details are described in relation to FIG. 12, below.

As seen in FIG. 7A, assembly 40 has packaging folds 26 and 27, separating assembly 40 into three folding segments, anterior segment 28, middle segment 29 and posterior segment 31. Folds 26 and 27 are omitted from FIG. 76 for simplicity.

In the embodiment of FIGS. 7A and 7B, cooling pad 3 has horseshoe-shaped chamber 18 in anterior segment 28, elongate, parallel and spaced apart chambers 17 and 19 in middle segment 29 and teardrop-shaped chamber 14 and horseshoe-shaped 16 in posterior segment 31. Horseshoe-shaped chamber 16 faces horseshoe-shaped chamber 18.

When worn, posterior segment 31 is placed abutting the anus and the middle segment 29 abuts the vulva—as depicted.

FIGS. 8A and 8B depict an assembly 50 with chambers located in anterior, middle and posterior segments (28, 29, 31) of the assembly, similar to assembly 40. However, the cooling pad 33 used is smaller and targeted specifically on areas for cooling, having inwardly facing horseshoe-shaped chamber 38 in anterior segment 28, and two elongate, S-curved or wishbone-shaped chambers 37 and 39 extending along the middle segment 29 and a terminating semi-circular chamber 36 in the posterior segment 31. The two elongate S-curved chambers 37, 39 frame a teardrop-shaped chamber 34 in middle segment 29. In use, assembly 50 is placed so that chambers 38, 37 and 39 are next to the vulva and teardrop-shaped chamber 34 is next to the anus.

Horseshoe-shaped chamber 38 in anterior segment 28 and semi-circular chamber 36 in posterior segment 31 could be interchanged, or substituted with near analogues as would be appreciated by those skilled in the art.

FIGS. 9A and 9B depict an assembly 60 having chambers only in anterior segment 28 and middle segment 29, reducing the number of segments having chambers. Cooling is also targeted specifically on the areas for cooling. In anterior segment 28 cooling pad 43 has a horseshoe-shaped chamber 32, facing a larger horseshoe-shaped chamber 35 in middle segment 29, having centred therein a teardrop-shaped chamber 41. As is evident, posterior segment 31 has no chamber. As worn, the vulva spans the anterior segment 28 and the middle segment 29, while the anus is over middle segment 29, towards the rear of horseshoe-shaped chamber 35.

Cooling pad 43 is a contraction of cooling pad 3, collapsed to the anterior and middle segments 28, 29. As is evident in cooling pads 3 and 43, the horseshoe-shaped chamber 16, 35 in the middle or posterior segment is larger than chamber 18, 32 in the anterior segment: the larger horseshoe-shaped chamber 16, 35 is about a third wider, and twice as long, as the smaller horseshoe-shaped chamber 18, 32.

The larger horseshoe-shaped chambers 16, 35 and the S-curved chambers 37, 39 frame a central teardrop-shaped chamber 14, 34, 41, which is oriented to fill partly the internal space defined by these outer chambers. This provides a uniform cooling sensation across the area.

FIGS. 10A, 10B and 10C relate to aspects of packaging of the assemblies of some of the different embodiments described above. As is most clearly evident from FIGS. 7A, 8A, 9A, the assemblies 40, 50, 60 are segmented into sections to permit ready folding into thirds, approximately among lines 26 and 27. This results in an approximately square-shaped packaging 70 as shown in FIGS. 10A to 10C.

FIG. 10A depicts any of assemblies 40, 50, 60 after having been folded into thirds and packaged in an outer cover 44, heat sealed at 45 and 46 in known manner. Included on cover 44 is a temperature-sensitive device 47. Device 47 changes visual appearance to indicate when assembly 40, 50, 60 is sufficiently cold for use. Device 47 has suitable temperature-sensitive ink/s and/or coatings, such as those available from Chromatic Technologies Inc., of Colorado, United States of America.

FIG. 10B depicts a small stack 48 of packaged assemblies 40, 50, 60 as depicted in FIG. 10A. FIG. 10C illustrates in cross-sectional view segmentation of each such assembly when folded into the packaging 44 of FIGS. 10A and 10B, per fold lines 26 and 27 indicated in FIGS. 7A, 8A, 9A.

Figure 11A:
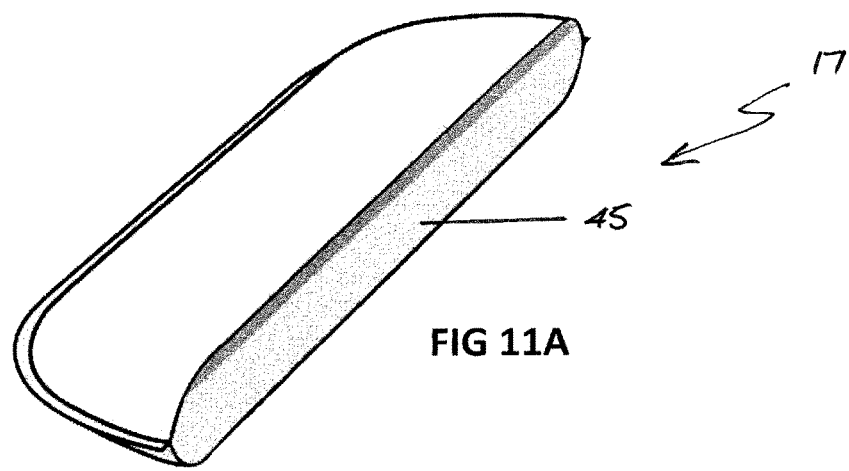
FIGS. 11A to 11C are schematic representations of cooling pack formats that may be used in connection with the embodiments depicted in connection with FIGS. 1 to 9.
Figure 11B:
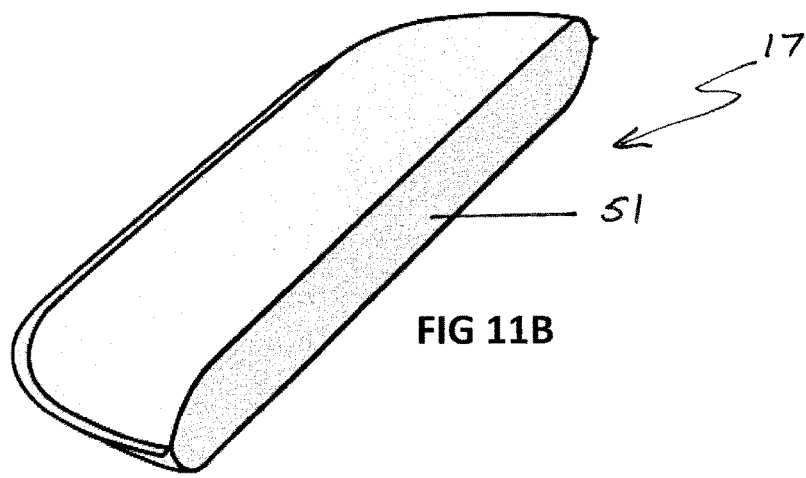
Figure 11C:
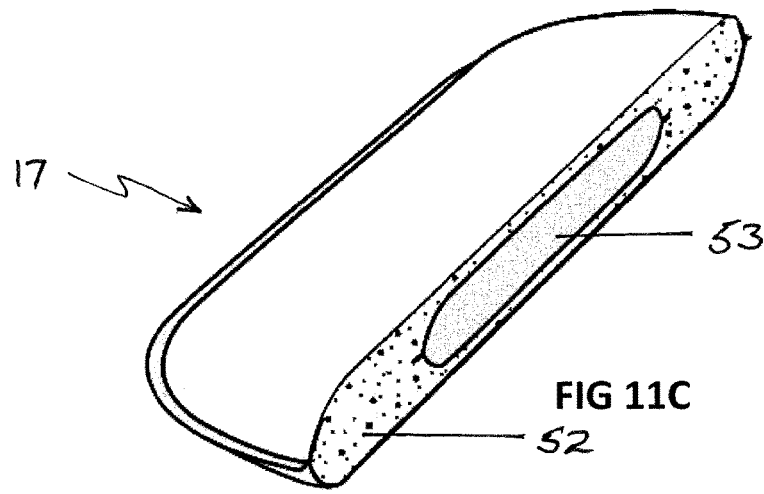

FIGS. 11A, 11B, 11C outline in cross-sectional view different constructional options for a chamber of a cooling pad of the invention, across different embodiments described herein. For convenience, the options are illustrated with regard to chamber 17 of cooling pad 3.

FIG. 11A depicts cooling option A: chamber 17 is filled with water or saline solution 45. This has the advantage of being a non-toxic affordable solution, which requires freezing before use.

FIG. 11B depicts cooling option B: chamber 17 is filled with a freezable gel, non-toxic 51. Gel 51 requires freezing before use and is reusable.

FIG. 11C depicts cooling option C: chamber 17 is filled with a urea 52 and in inner water-filled tube 53, which is a non-toxic instant cooling combination not requiring freezing. When chamber 17 is manipulated to break inner water-filled tube 53, the resulting endothermic reaction with urea 52 causes cooling.

As will be appreciated, each of these options offers its own advantages and compromises.

Figure 12:
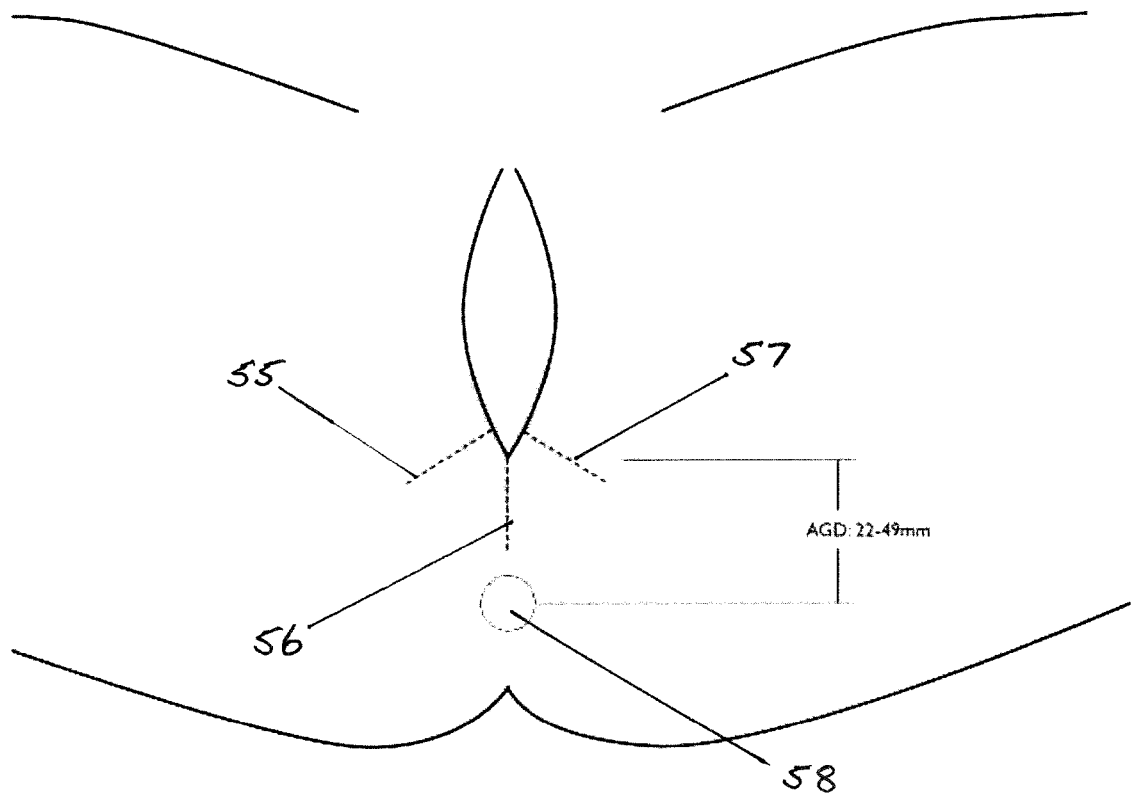
FIG. 12 illustrates the main areas of the perineum needing alleviation of pain or discomfort after vaginal delivery.

FIG. 12 shows schematically the main areas needed for cooling post birth. These include perineal tearing (1st, 2nd, 3rd and 4$^{th}$ degree tears), possible episiotomy, indicated at 55, 56 and 57, and general selling (not labelled).

Anogenital distance (AGD) is measured for women from the anus 58 to the base of the vagina and as indicated in FIG. 12 is roughly between 22 mm and 49 mm, based on the AGD distances described in two studies of women of reproductive age [1, 2].

In order to adequately cover the areas needed for as many women as possible, an average anogenital distance of 40 mm was used for the cooling pad designs described above.

Figure 13:
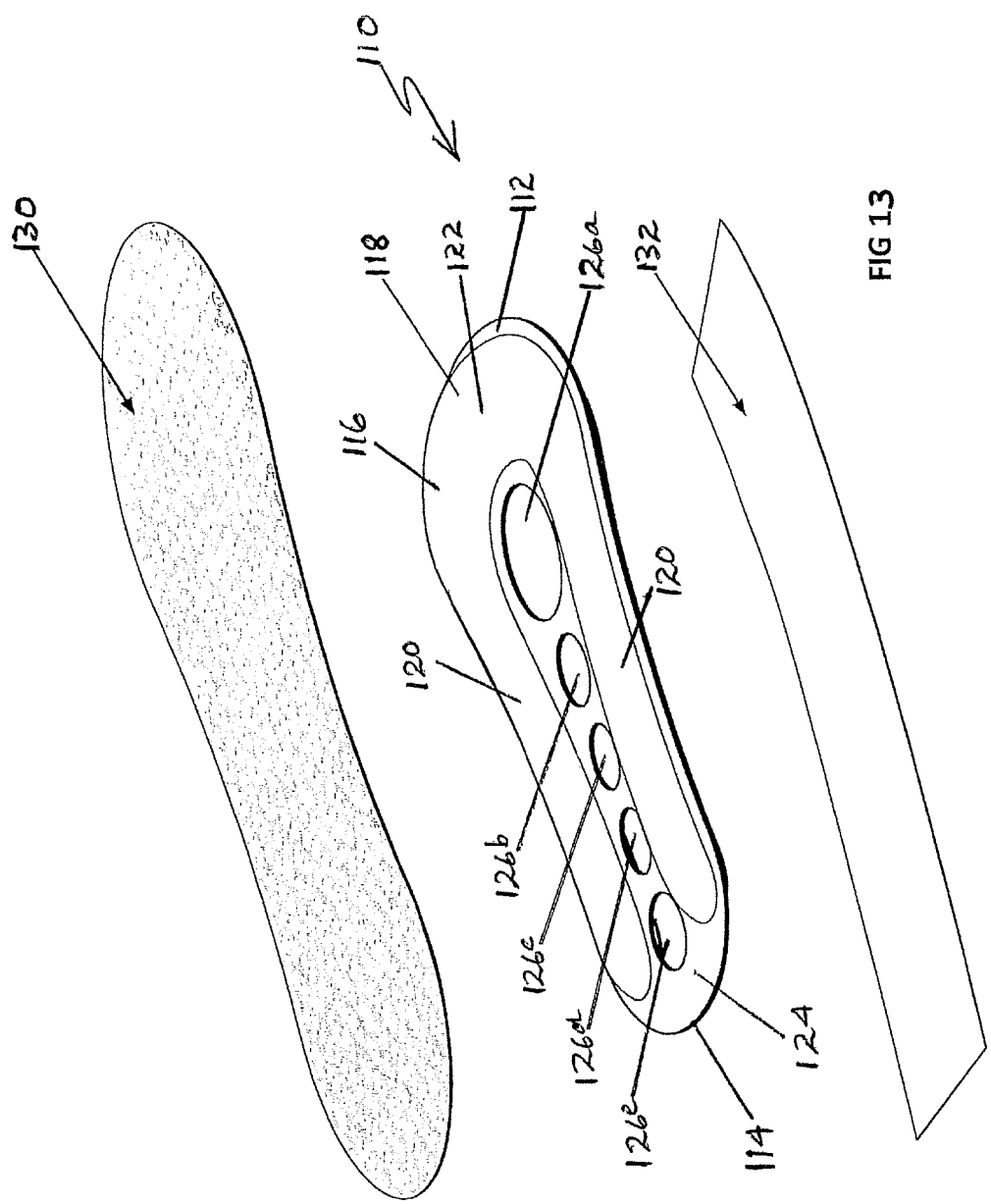
FIG. 13 is an exploded perspective view of components of a cooling pad assembly according to a further embodiment of the present invention, which includes a cover layer and a peel-off backing in an assembly.

Referring now to FIG. 13, cooling pad 110 has an anterior end 112 and a posterior end 114. Chamber 116 contains saline solution for cooling and has a first volume 118 at anterior end 112 and a pair of second volumes 120 between anterior end 112 and posterior end 114. In this embodiment, first volume 118 is not partitioned from second volumes 120.

Chamber 116 is approximately horseshoe-shaped. First volume 118 is located at the head 122 of the horseshoe, with second volumes 120 forming the legs.

Web 124 is formed between the pair of second volumes 120 and has five apertures 126a to 126e to allow passage of body fluid.

Cooling pad 110 may be used alone. However, in this embodiment, cooling pad 110 is part of an assembly, sandwiched between cover layer 130 and peel-off backing 132, and intended to be placed in a freezer or refrigerator prior to use.

Cover layer 130 is adhered to cooing pad 110 by adhesive (not shown). As can be seen in FIG. 13, cover layer 130 is contoured to fit the body, as is cooling pad 110. Cover layer 130 may incorporate wings if desired.

Adhesive (not shown) on the underside of cooling pad 110 can be used to adhere cooling pad 110 to underwear (not shown) by removing peel-off backing 132.

Figures 14, 15:
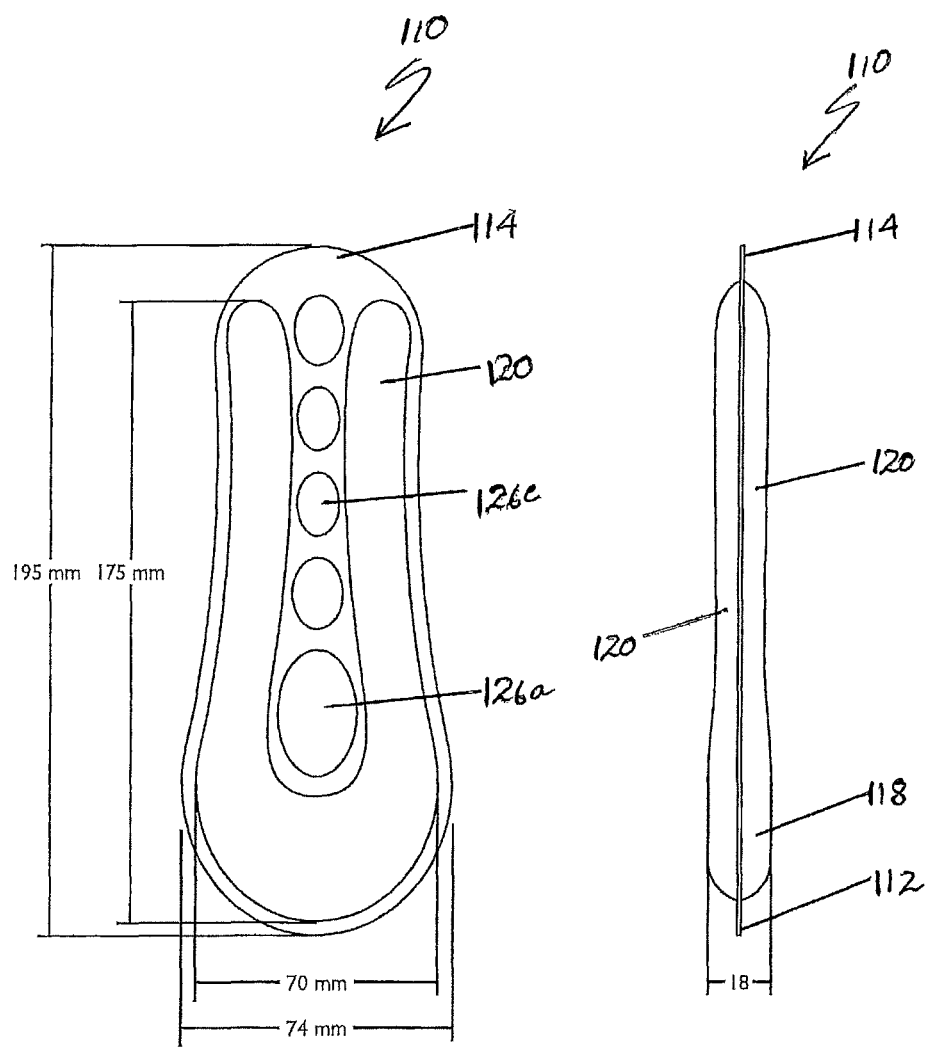
FIG. 14 is a plan view from above of the cooling pad included in FIG. 13.
FIG. 15 is a side view of the cooling pad shown in FIG. 14.

Turning now to FIGS. 14 and 15, dimensions of an exemplary version of cooling pad 110 are set out. In this embodiment, chamber 116 contains 78 ml of saline solution.

Figure 16:
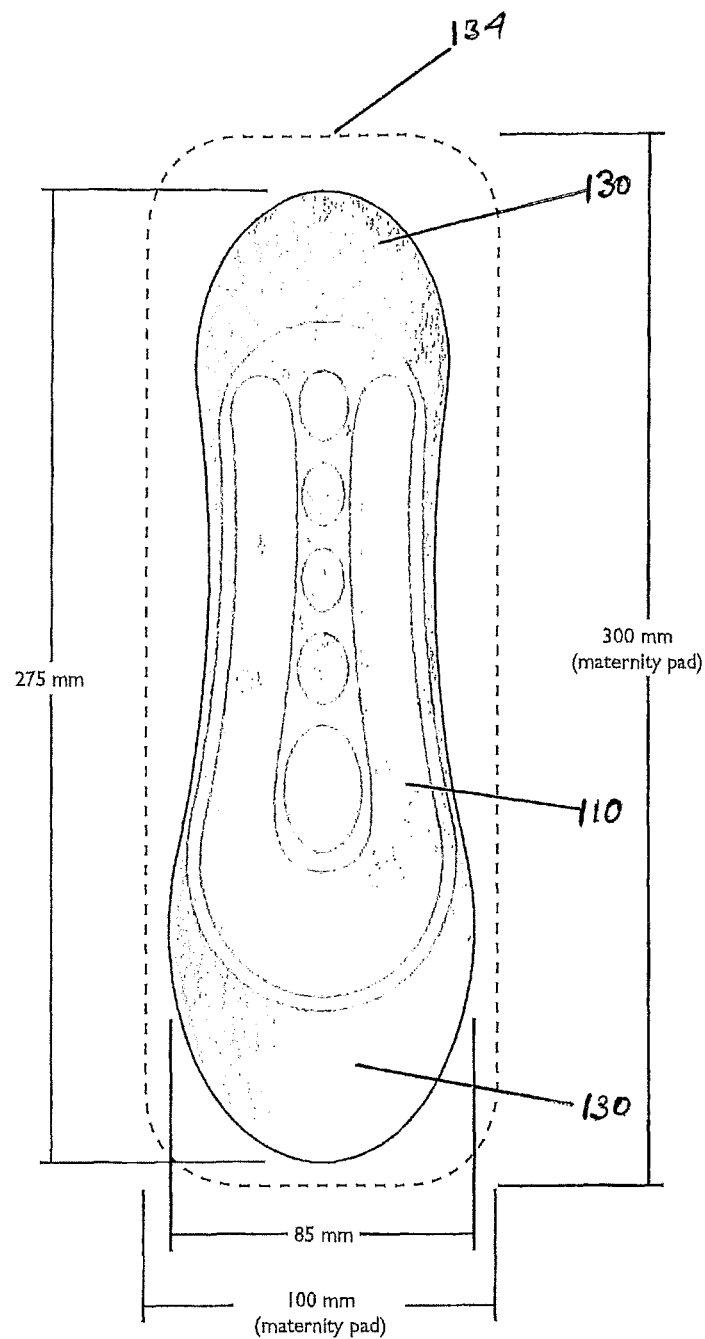
FIG. 16 is a plan view of the assembly of FIG. 13, superimposed upon a maternity pad.

In FIG. 16, the assembly of FIGS. 13 to 15 is shown superimposed on a maternity pad 134 (shown in dashed outline), with dimensions. Cooling pad 110 is adhered to maternity pad 134 after peel-off backing 132 is removed to expose adhesive (not shown).

Figure 17:
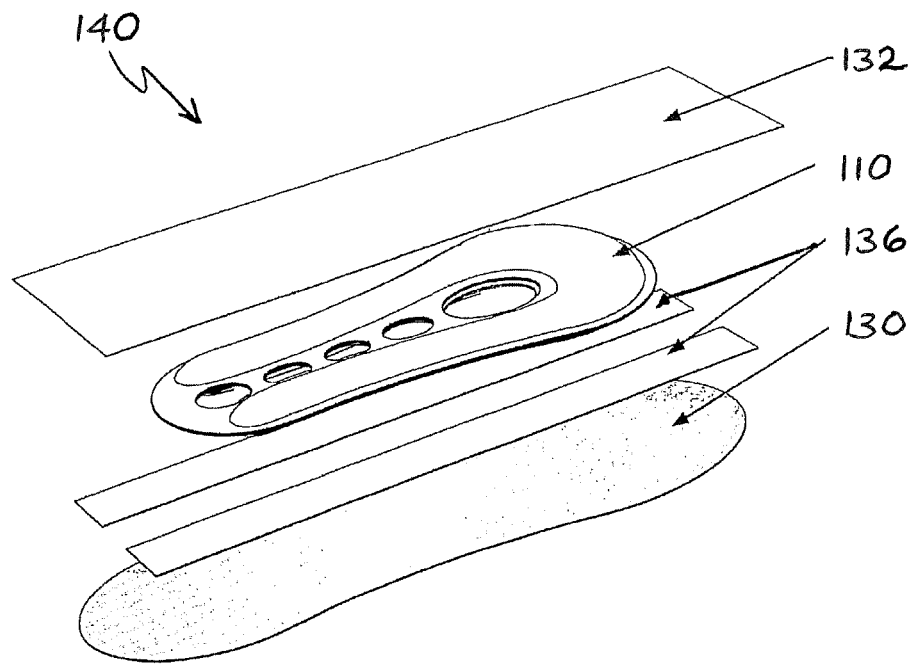
FIG. 17 is a perspective exploded view of another embodiment of a cooling pad assembly where adhesive strips are located on the cover layer.
Figure 18:
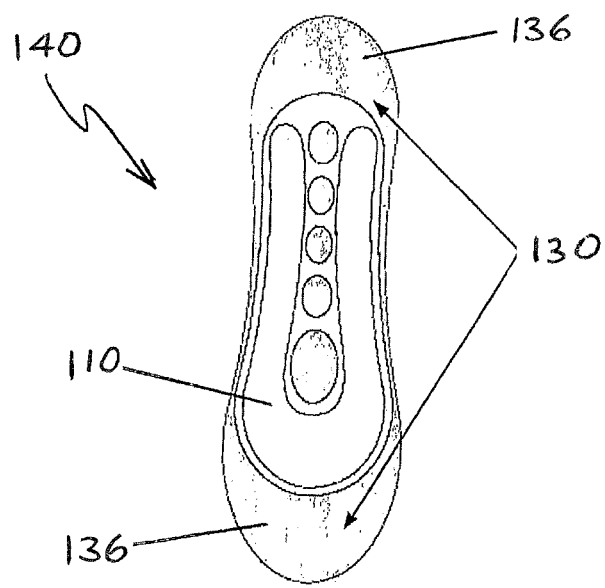
FIG. 18 is a plan view from below of the assembly of FIG. 17.

FIGS. 17 and 18 illustrate a second form of assembly, 140. The same labels are used to denote the same or equivalent components. Assembly 140 has cooling pad 110, cover layer 130 and peel-off backing 132 which are the same as in the previous FIGS and which will not be described in detail again. In assembly 140 there are adhesive strips 136 which are longer than cooling pad 110. Consequently, when assembly 140 is assembled as shown in FIG. 18, adhesive strips 136 extend beyond cooling pad 110 and are available to adhere assembly 140 to underwear or a maternity pad. It is to be noted that adhesive strips 136 are spaced apart so as not to impede body fluids travelling through cover layer 130 and apertures 126 in cooling pad 110.

Figure 19:
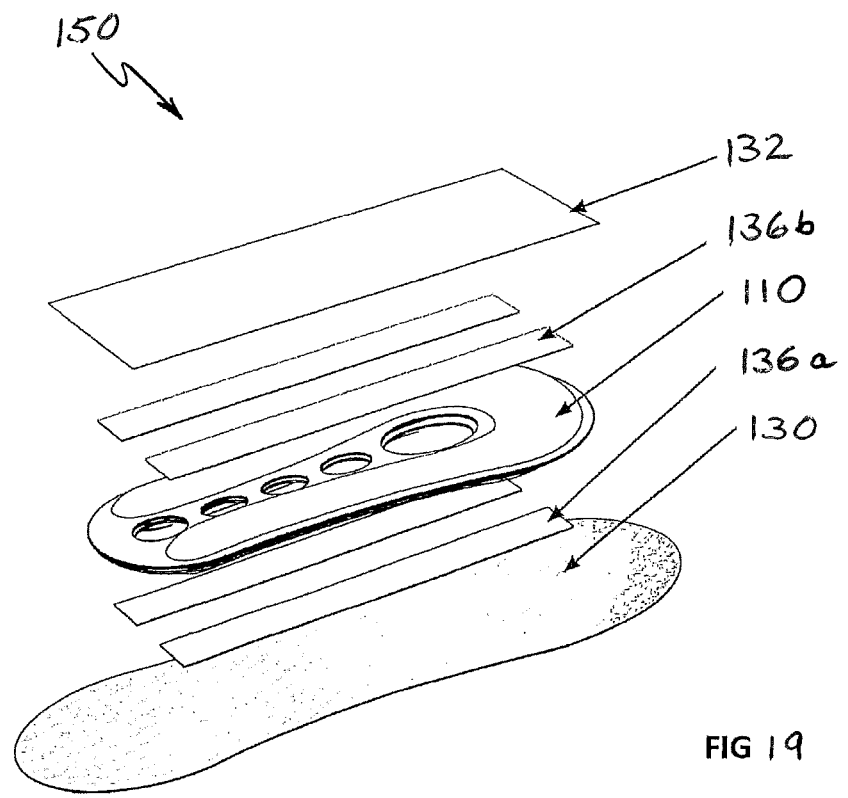
FIG. 19 is a perspective exploded view of a further embodiment of a cooling pad assembly where adhesive strips are located on both sides of the cooling pad.
Figure 20:
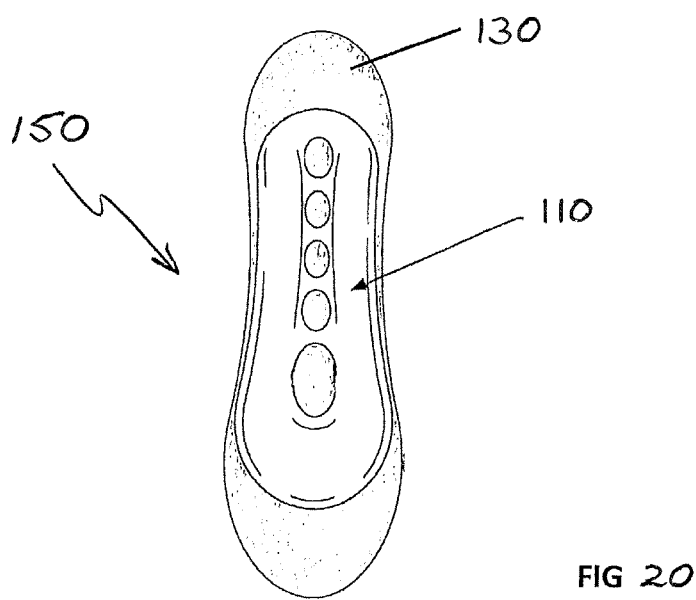
FIG. 20 is a plan view from below of the assembly of FIG. 19.

FIGS. 19 and 20 illustrate a third form of assembly, 150. The same labels are used to denote the same or equivalent components. Assembly 150 has cooling pad 110, cover layer 130 and peel-off backing 132 which are the same as in the previous FIGS and which will not be described in detail again. In assembly 150 there are adhesive strips 136a and 136b. Two adhesive strips 136a are located between cooling pad 110 and cover layer 130. Two adhesive strips 136b are located between cooling pad 110 and peel-off backing 132. In contrast to assembly 140, adhesive strips 136a, 136b are a little shorter than cooling pad 110. When assembly 150 is assembled as shown in FIG. 20, two adhesive strips 136a adhere cover layer 130 to cooling pad 110 and two adhesive strips 136b adhere to cooling pad 110. When backing layer 132 is peeled off, adhesive strips 136b are available to adhere assembly 150 to underwear or a maternity pad. As before, adhesive strips 136a, 136b are spaced apart so as not to impede body fluids travelling through cover layer 130 and apertures 126 in cooling pad 110.

Figure 23:
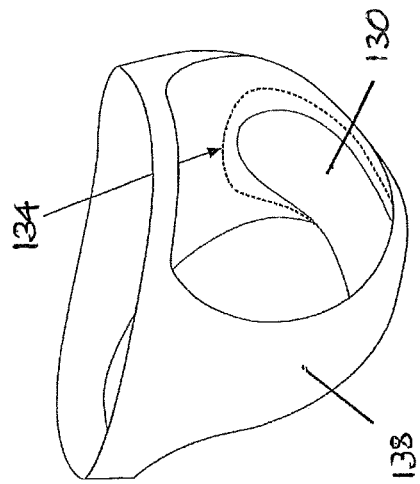
FIGS. 21 to 23 are representations of an embodiment of a method of use of the cooling pad of the invention.
Figure 22:
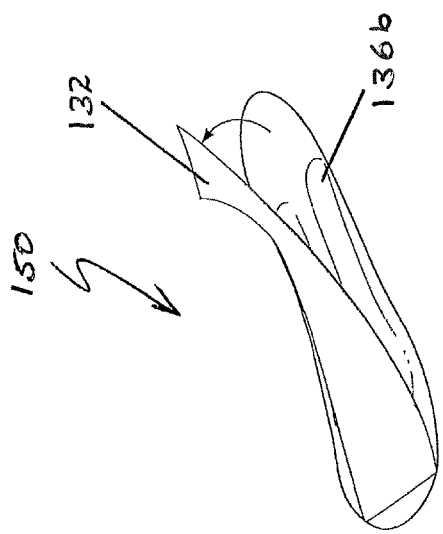
Figure 21:
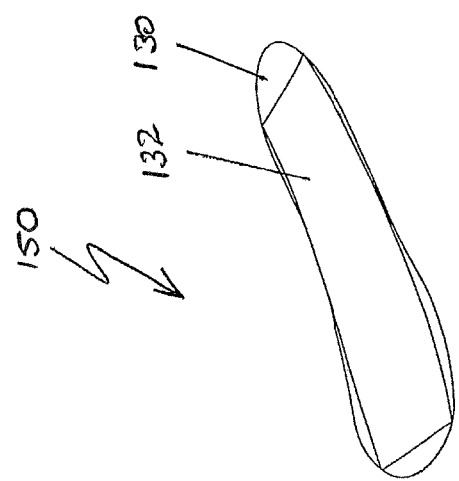

FIGS. 21 to 23 illustrate how an assembly according to the present invention may be utilised. Reference is made to assembly 150, shown in FIGS. 19 and 20, but the method of use can apply to other embodiments.

Assembly 150 is first chilled or frozen before use. When it is required, assembly 150 is removed from any packaging (FIG. 10A). Peel-off backing layer 132 is removed, exposing adhesive strips 136b (FIG. 22). Assembly 150 is turned over so that adhesive strips 136b face downwards and positioned onto a maternity pad 134 or underwear 138 (FIG. 23), as desired.

Figure 24:
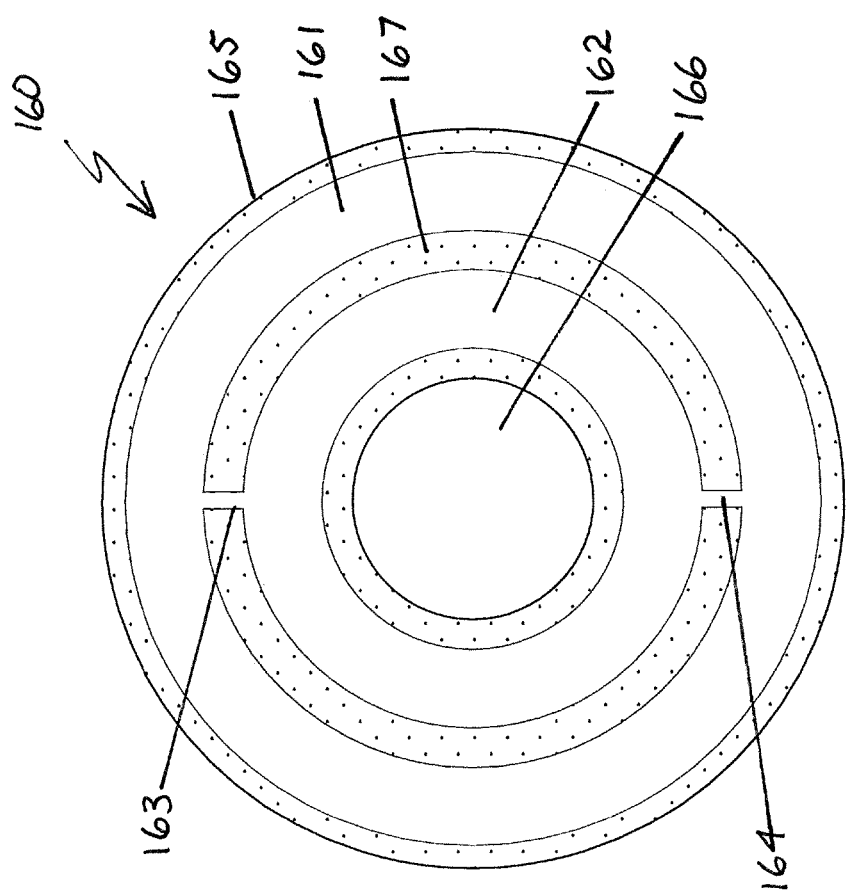
FIG. 24 shows a plan view of a mastitis pad according to the invention.

An embodiment of a cooling pad 160 suitable for use as a mastitis pad is shown in FIG. 24. Cooling pad 160 two concentric chambers 161 and 162, joined at passages 163 and 164. In an alternate embodiment, passages 163 and 164 may be omitted. Chamber 161 lies along periphery 165.

At the centre of cooling pad 160 is a single aperture 166, formed in web 167. Web 167 also joins chambers 161 and 162. Aperture 166 is inboard of chambers 161 and 162.

Figure 25:
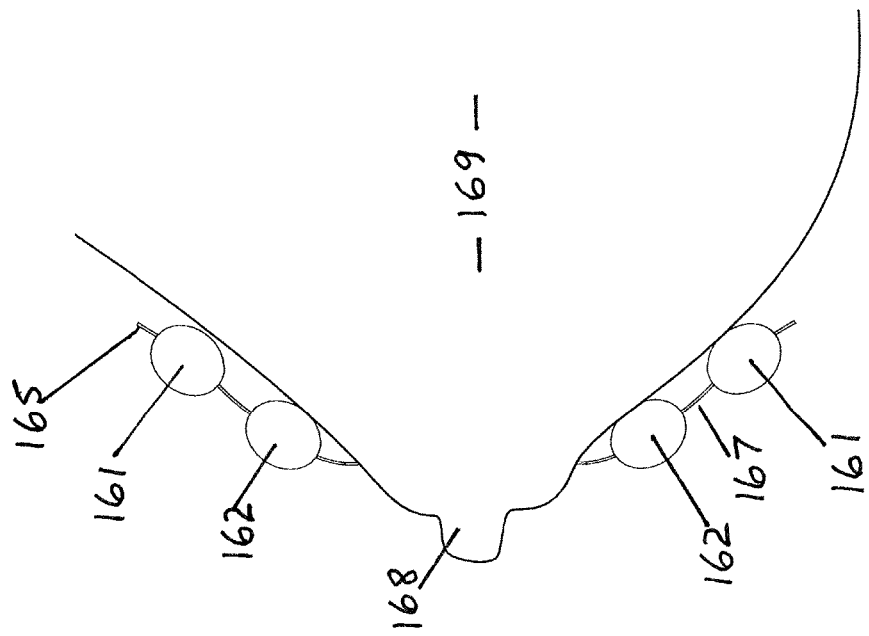
FIG. 25 is a side elevation cross-sectional schematic view of the pad of FIG. 24.

As may be seen from the schematic cross-sectional view in FIG. 25, aperture 166 is sized to accommodate a nipple 168 of breast 169.

Each of the embodiments described above has included at least one aperture for allowing passage of body fluid, the aperture being located inboard of the one or more chambers. The embodiments below are of the second aspect of the invention: a cooling pad for perineum relief, the pad having an anterior end and a posterior end, and including one or more chambers, containing a fluid for cooling, located on a web.

FIG. 26 shows in plan view cooling pad 170 having an anterior end 171 and a posterior end 172. In this embodiment, cooling pad 170 has a single chamber 173, supported by web 174. Web 174 and chamber 173 are generally teardrop-shaped. The first or larger volume of chamber 173 is located near posterior end 172. Chamber 173 is located close to periphery 175 and travels around it. Chamber 173 encloses part of web 174, as shown.

Cooling pad 170 may be provided with a soft and thin absorption layer 11, like that in FIG. 3 but teardrop-shaped. Cooling pad 170 may also have adhesive strips as described above to enable attachment to clothing. Cooling pad 170 may be used to alleviate pain or discomfort in the perineum caused by cycling.

A second embodiment of a cycle pad is shown in FIGS. 27 and 28. Cooling pad 180 has an anterior end 181 and a posterior end 182, being of the same shape as anterior end 181. In this embodiment, cooling pad 180 has a four linked chambers 183, 184, 185 and 186, supported by web 187, a non-woven fabric. The chambers 183, 184, 185 and 186 are made of plastic and filled with saline solution.

As shown in FIG. 28, cooling pad 180 is provided in an assembly having a top layer 188 being a non-woven fabric bonded to plastic, an under layer 189 of the same materials and four adhesive strips 176 for attaching the assembly to clothing.

The embodiment in FIGS. 29 to 31 is suitable for use for alleviating pain or discomfort in the perineum following vasectomy or prostate invasion. Cooling pad 190 has three parallel chambers 191, 192 and 193 located on web 194. As illustrated in FIG. 30, the three parallel chambers 191, 192 and 193 allow pad 190 to contour to body shape in use, as indicated by the arrows.

Cooling pad 190 can be inserted into an assembly as shown in FIGS. 31 and 32, in a similar way to the embodiment in FIG. 6. The assembly has an upper non-woven fabric layer 195, and a lower non-woven fabric layer 196 with elasticised strips 197. Layer 195 is bonded to layer 196, as shown by dotted line 198, leaving an opening 199 (FIG. 32) through which cooling pad 190 is inserted after it has been chilled or frozen to the desired temperature. Adhesive strips 176 can be used to attach the assembly to clothing.

Elasticised strips 197 enable the sides of the assembly to fit snugly, as shown in FIG. 32. Cooling pad 190 may be reused, while the remainder of the assembly may be discarded after use.

The cooling pads of the invention may be made of any suitable materials. Preferred materials are nylon or polyethylene for the plastic base layer and Fixomull (trade mark) or similar material for the soft upper layer, known for manufacture of personal care and wound care products. The preferred Fixomull product is available as Fixomull Stretch from, for example, BSN Medical, of Mount Waverley, Victoria, Australia. Fixomull Stretch is a hypoallergenic, porous, adhesive, non-woven tape, especially suitable for use on frequently mobile and highly contoured parts of the body. It is made from a white, stretchable, non-woven polyester dressing sheet coated with skin-friendly polyacrylate adhesive on quick-release backing paper. In the embodiment in FIG. 13, for example, top layer 130 may be made from Fixomull Stretch and adhered to cooling pad 110, using the polyacrylate adhesive.

Where required, bonding may take place by lamination, using heat sealing. Chambers may be filled with cooling fluid while the chambers are undergoing sealing.

A preferred cooling fluid is saline solution, a hypotonic 7% salt solution. It is preferred that each chamber is of maximum volume 70 to 80 ml. A preservative or antibacterial may be included for longer shelf life, as may be a dye.

Using a hypertonic 7% saline solution, the cooling pad of the invention may be cooled to −4 degrees Celsius without freezing. In suitable embodiments, the cooling pad, if cooled to −4 degrees Celsius, is capable of providing relief in the range −4 degrees to +4 degrees Celsius, for at least 30 minutes.

It will be appreciated that the embodiments of the invention described above are not intended to be limiting on the scope of the invention. Variations are within the spirit and scope of the invention.

The invention claimed is:

1. A cooling pad for alleviation of pain or discomfort, the pad including:
    an anterior end and a posterior end;
    one or more chambers, containing a fluid for cooling, the one chamber, or a plurality of the chambers together, forming a head and two legs in an approximately horseshoe configuration, with a first chamber located at the head of the horseshoe; and
    a web extending between the head and legs of the horseshoe; wherein the first chamber located at the head of the horseshoe is at the anterior end; and wherein at least one aperture is formed in the web and located in an area between the head of the horseshoe and the two legs, the aperture being adapted to allow passage of body fluid through the pad, the aperture having a boundary surrounded by the web.

2. The cooling pad of claim 1, wherein the web has a plurality of the apertures located in the area.

3. The cooling pad of claim 2, wherein the apertures are of different sizes.

4. The cooling pad of claim 1, wherein the first chamber is not partitioned from chambers forming the legs of the horseshoe configuration.

5. The cooling pad of claim 4, which includes a chamber having a volume of fluid for cooling, the chamber having the volume of fluid for cooling being located at the posterior end of the pad.

6. The cooling pad of claim 4, which includes a further chamber having a volume of fluid for cooling, the further chamber being located posteriorly of the first chamber.

7. The cooling pad of claim 1, adapted for perineum relief.

8. The cooling pad of claim 1, wherein the cooling fluid is a saline solution, adapted for freezing.

9. The cooling pad of claim 1, which includes a cover sheet.

10. The cooling pad of claim 1, which includes adhesive means.

11. The cooling pad of claim 1, further including an absorbent pad.

* * * * *

UNITED STATES PATENT AND TRADEMARK OFFICE
CERTIFICATE OF CORRECTION

| | | |
|---|---|---|
| PATENT NO. | : 11,957,618 B2 | Page 1 of 1 |
| APPLICATION NO. | : 16/470664 | |
| DATED | : April 16, 2024 | |
| INVENTOR(S) | : Antoinette Campbell, Kylee Callow and Natalie Wearne | |

It is certified that error appears in the above-identified patent and that said Letters Patent is hereby corrected as shown below:

In the Claims

Claim 5, Column 10, Line 47, please delete the phrase "according to claim 4" and replace with "according to claim 1".

Signed and Sealed this
Thirty-first Day of December, 2024

Derrick Brent
*Acting Director of the United States Patent and Trademark Office*